US 6,662,040 B1

(12) United States Patent
Henrichs et al.

(10) Patent No.: US 6,662,040 B1
(45) Date of Patent: Dec. 9, 2003

(54) METHODS OF PHOTOACOUSTIC IMAGING

(75) Inventors: Paul Mark Henrichs, Houston, TX (US); Marten Eriksen, Oslo (NO); Pal Rongved, Oslo (NO); Wolfgang Hans Heinrich Gunther, West Chester, PA (US); Robert Allen Snow, West Chester, PA (US); Kenneth Robert Hollister, Chester Springs, PA (US); Gregory Lynn McIntire, West Chester, PA (US); Steven Blair Coffey, Pawcatuk, CT (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/458,008

(22) Filed: Dec. 10, 1999

Related U.S. Application Data

(63) Continuation of application No. PCT/GB98/01751, filed on Jun. 16, 1998.
(60) Provisional application No. 60/049,909, filed on Jun. 18, 1997.

(30) Foreign Application Priority Data

Jun. 16, 1997 (GB) ............................................. 9712524

(51) Int. Cl.$^7$ ................................................. A61B 6/00
(52) U.S. Cl. ..................... 600/431; 600/407; 600/410; 600/436; 600/437; 600/473; 600/476; 424/9.2; 424/9.3; 424/9.52; 424/9.6
(58) Field of Search ................................ 600/310, 312, 600/321, 329, 407, 410, 436, 437, 458, 473, 476, 431; 424/82.05, 9.52, 9.6, 9.2, 9.3

(56) References Cited

U.S. PATENT DOCUMENTS

| 4,267,732 | A | * | 5/1981 | Quate ........................... 73/606 |
| 4,385,634 | A | | 5/1983 | Bowen |
| 4,442,843 | A | | 4/1984 | Rasor et al. |
| 5,492,840 | A | * | 2/1996 | Malmqvist et al. .......... 436/518 |
| 5,719,027 | A | * | 2/1998 | Miyazaki et al. ............... 435/6 |
| 5,840,023 | A | * | 11/1998 | Oraevsky et al. ............ 600/407 |
| 6,022,309 | A | * | 2/2000 | Celliers et al. ................. 600/7 |
| 6,123,923 | A | * | 9/2000 | Unger et al. ................ 424/9.52 |
| 6,309,352 | B1 | * | 10/2001 | Oraevsky et al. ............... 367/7 |

FOREIGN PATENT DOCUMENTS

| EP | 0 826 377 A | 3/1998 |
| WO | WO 96 17628 A | 6/1996 |

OTHER PUBLICATIONS

Inga–Mai Tegmo–Larsson et al., "Phytochrome Models. 6. Conformation Control by Membrane of Biliverdin Dimethyl Ester Incorporated into Lipid Vesicles." Journal of the American Chemical Society, 1981, XP002082767.

(List continued on next page.)

Primary Examiner—Marvin M. Lateef
Assistant Examiner—Jeoyuh Lin
(74) Attorney, Agent, or Firm—Bacon & Thomas

(57) ABSTRACT

The invention relates to a method of generating an image of an animate human or non-human animal body or part thereof. The method comprises administering to said body a physiologically tolerable contrast agent comprising a radiation absorbing component and/or a pressure inducing component, exposing said body to radiation, detecting pressure waves generated in said body by said radiation and generating an optoacoustic image therefrom of at least a part of said body containing the administered contrast agent.

48 Claims, 3 Drawing Sheets

BIODISTRIBUTION OF NC 100448 IN FEMALE IMMUNODEFICIENT MICE WITH HT-29 TUMORS ONE HOUR POST-DOSING

OTHER PUBLICATIONS

K. Giese et al., "Photoacoustic in vivo Study of the Penetration of Sunscreen into Human Skin.", Can. Journal of Physics, 64:9, Sep. 1986, XP002082768.

F. Lenci et al., "Spectroscopic and Photoacoustic Studies of Hypericin Embedded in Liposomes as a Photoreceptor Model," Photochemistry and Photobiology, 62:1, 1995, XP002082769.

Chemical Abstracts, 119:11, Sep. 13, 1993, Columbus, Ohio, Niedbalska, Malgorzata et al., "Incorporation of stilbazolium, merocynaines into biological membranes", ZP002082770.

Database Medline U.S. National Library of Medicine (NLM), Bethesda, MD, Andreoni A. et al., "Quantitative Measurements of Porphyrin Pigments in Tissues via Photoacoustic Sepctroscopy," XP002082771 and Journal of Biochemical and Biophysical Methods, Mar. 1990.

* cited by examiner

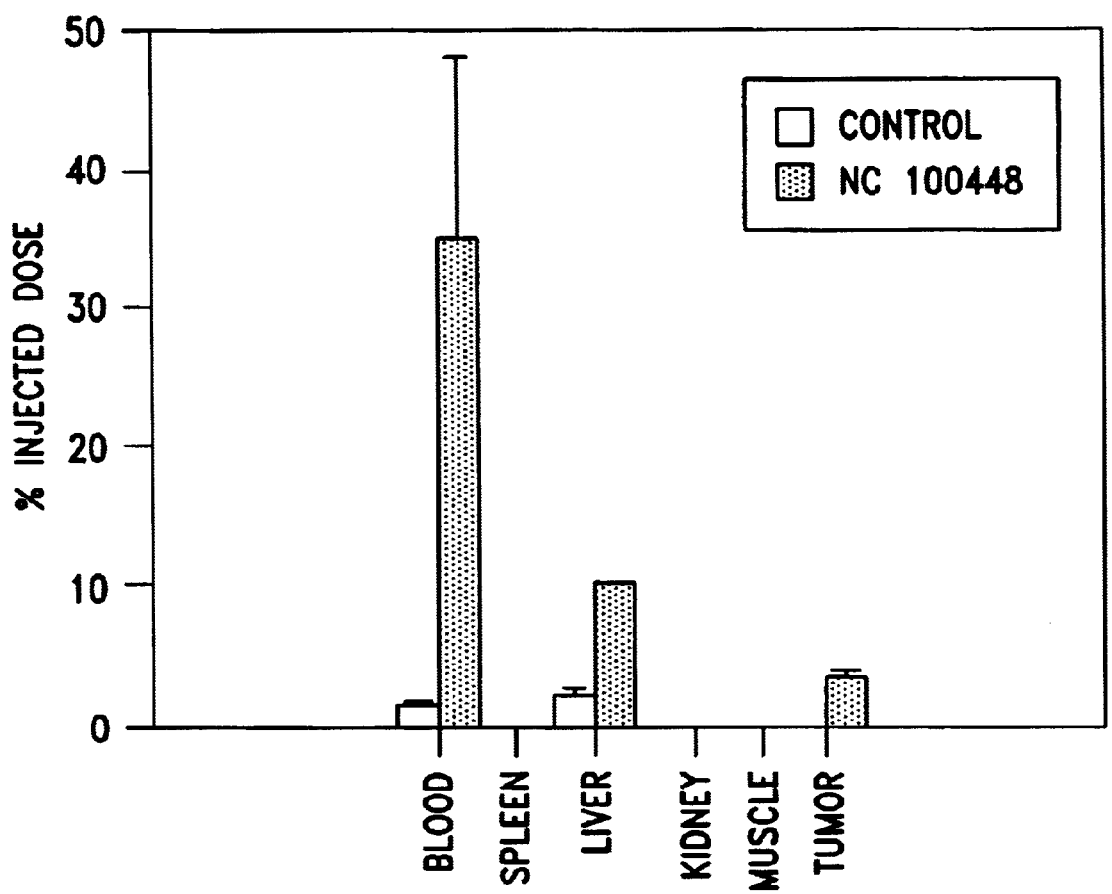

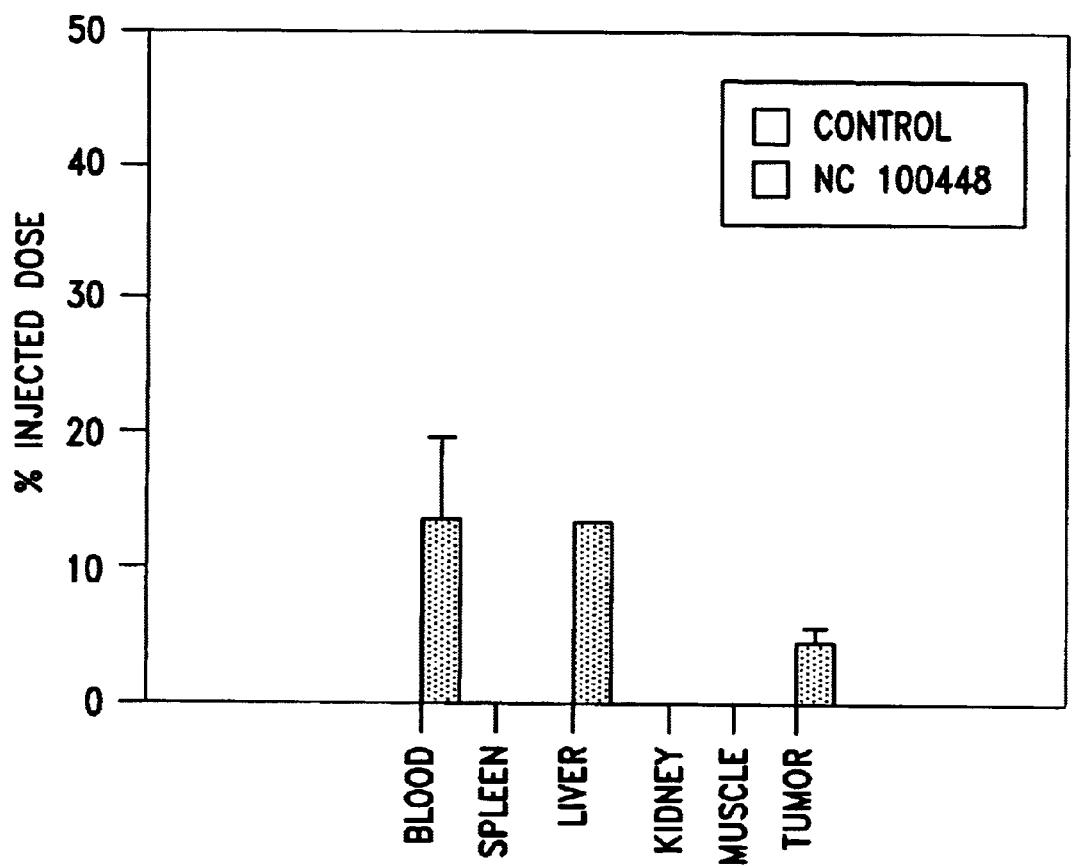

METHODS OF PHOTOACOUSTIC IMAGING

This application is a continuation of pending international application number PCT/GB98/01751 filed Jun. 16, 1998 (of which the entire disclosure of the pending, prior application is hereby incorporated by reference), which itself is a continuation-in-part of U.S. provisional application No. 60/049,909 filed Jun. 18, 1997.

The present invention relates to the use of contrast agents to achieve contrast enhancement in in vivo photoacoustic imaging of human or non-human animal subjects.

Energetic radiation incident on certain materials is absorbed. When absorption results in heat output, there is a local rise in temperature. The temperature returns to that of the surroundings after the irradiation ceases. If the incident radiation is a sharp pulse, heat propagates from the absorption site as a thermal wave, which may be converted into a pressure pulse on contact with a suitably expanding medium (for example, a gas at the surface of the sample). When the incident irradiation varies in intensity at a characteristic frequency, there is periodic heating and cooling at the absorbing site that translates to periodic heating and cooling at the surface accompanied by periodic pressure changes at the surface. These can be detected as sound that has a fundamental frequency equal to that of the intensity variation of the incident radiation.

Whether the thermal wave reaches the surface after a pulse of light is determined by the thermal diffusivity and thickness of the sample. The detection of. sound waves actually generated at the sample surface is therefore generally only suitable for very thin samples. However, if the absorbing site expands sufficiently following light absorption, sound can also be produced directly at the interface between the absorbing site and the surrounding medium. When the incident radiation is a sharp pulse, the pressure increase produced by expansion of the absorbing site is temporary, but nevertheless a pressure disturbance propagates at the speed of sound from the absorbing site following the pulse. This can be detected with a transducer at some distance from the absorbing site as a time-dependent change in pressure. The elapsed time between the initial irradiation and the arrival of the pressure disturbance at the detector provides an indication of the distance of the absorbing site from the transducer. The shape of the detected pressure disturbance provides information about the shape of the incident pulse and the shape of the absorbing site. The time-domain signal is equivalent to a distribution of sound waves of different frequencies in the frequency domain. The shape of the distribution and the phases of the individual frequencies in the distribution are determined by the length of the irradiating pulse, the shape of the absorbing site, its distance from the point of detection, and the sonic properties of the medium.

When the intensity of the incident radiation varies periodically with a characteristic frequency, there is a corresponding rise and fall in the pressure imposed on the surrounding medium by the absorbing site. The pressure changes radiate throughout the sample as sound with fundamental and harmonic frequencies equal to those of the incident radiation. Detection at the frequency at which the incident radiation varies permits direct determination of one point in the frequency domain. In principle, the entire distribution in the frequency. domain can be found by making measurements at many different frequencies.

The generation of sound waves by incident radiation is known as the "photoacoustic" or "optoacoustic" effect and is reviewed by Tam (Reviews of Modern Physics, 1986, 58(2), p381–431). We use the two words interchangeably to refer to this phenomenon.

The incident radiation may be any type of energetic radiation, including electromagnetic radiation from radiofrequency to X-ray, electrons, protons, ions, and other particles. For simplicity, all of the above will be referred to herein as "radiation". The word "light" will be used specifically to denote electromagnetic radiation of any wavelength or frequency.

Photoacoustic spectroscopy has been used as a sensitive means of detecting trace impurities in gases, and has developed into a useful analytical tool for the sensitive detection of chemical species in liquids and solids, within powders, or in highly turbid liquids, where severe light scattering would interfere with direct methods of spectroscopy (for example, see Rosencwaig, 1975, Anal. Chem., 47(6), p592A–604A; Karabutov et al., 1995, SPIE, 2389, p209–216).

Photoacoustic methods can be used for the determination of both the optical and physical properties of materials. The efficiency with which radiation is converted into heat and pressure within the material depends on its optical properties. The propagation of thermal, pressure or sound waves depends on the mechanical and physical properties. Thus, the photoacoustic signals carry information about the elasticity, density, thickness of component regions, thermal conductivity and specific heat, as well as the optical properties of the material in which they are generated. They can also provide data about the crystallinity of solid and semi-solid samples and can be used to detect phase transitions and discontinuities. When the light beam is focused, some of these properties can be measured locally. Localization of properties in a lateral plane, across a sample, is the basis of photoacoustic microscopy.

Photoacoustic depth profiling can be performed when the measured sound wave is analysed in terms of transit time from the site of light absorption back to the detector. Signals from deep within a sample take longer to reach the detector than those from regions near the surface. For pulsed irradiation the longer transit time translates into a larger separation between the time of arrival of the pulse and the arrival of the signal at the detector. For amplitude-modulated irradiation, the longer transit time translates into a phase change in the detected sound wave. Together photoacoustic microscopy and photoacoustic depth profiling constitute photoacoustic imaging.

The use of short bursts of light (chopped light) rather than continuously applied light is especially helpful for photoacoustic depth profiling. In this case, the absorption of each light pulse and subsequent heating of the various regions of the sample produces one or more positive or negative pressure waves that propagate radially from the site of absorption after each pulse. For very short light pulses, the shape of the pressure pulses generated by the light pulses is determined by the optical and thermal properties, sizes and shapes of the different regions of the sample, as well as by the speed of sound within the sites and the surrounding medium (see for example, Karabutov et al., 1996, Appl. Phys., 63, p545–563; Hutchins, 1986, Can. J. Phys., 64, p1247–1264).

For exemple, in an absorbing sample measuring 5 mm, the stress (pressure wave) signal persists at the detector for several microseconds. Mathematically, a single sharp pulse that is several microseconds broad in time can be decomposed through Fourier transformation into a continuous distribution of multiple sine waves ranging in frequency from 0 to megahertz. Even though sound in the form of a sinusoidal time dependent pressure wave is absent, detection of the pressure pulses still requires ultrasound transducers. The term "photoacoustic" and its synonym "optoacoustic" are still appropriate because the detected signals are a composite of normal sound waves.

Photoacoustic spectroscopy has also been applied to clinical and biological analysis. For example, cancerous cells have been detected in urine (Huang et al., 1990, J. Biomed. Eng., 12, p425–428). Depth profiling has also been performed. For example, studies have been made of the retina (Boucher et al., 1986, Applied Optics, 25(4), p515–520), skin (Giese et al., 1986, Can. J. Phys., 64, p1139–1141), the cockscomb of a rooster (Oraevsky et al., 1995, SPIE,-2389, p198–208), leaves (Nery et al., 1987, Analyst, 112, p1487–1490; Kirkbright et al., 1984, Analyst, 109, p1443–1447), lichen (O'Hara et al., 1983, Photochemistry & Photobiology, 38(6), p709–715) and on tissue equivalents (Kruger & Liu, 1994, Am. Assoc. Phys. Med., 21(7), p1179–1184; Esanaliev et al., 1996, SPIE, 2676, p84–90; Oraevsky et al., 1996, SPIE, 2676, p22–31). In each case, the presence of areas of the sample which absorbed radiation of different wavelengths or absorbed more efficiently than background were detected at different levels within the samples. The generality of these methods have however been limited to only thin samples (in the order of a few cm) owing to the depth limitation of irradiation and the damping of sound waves as they pass through the sample to the detector.

Thus, sound waves produced within a sample, e.g. a body, must have sufficient amplitude to be detected at the surface of the sample after passing through any portions of the sample not contributing to the generation of the wave.

The use of photoacoustic spectroscopy for medical imaging has up to now had severe limitations. Not only was the detection of radiation absorbing objects normally possible only in very thin samples, but the method was also restricted to the detection of objects or materials within samples which absorbed radiation and produced the thermal waves required for the photoacoustic effect. These radiation absorbing regions had necessarily to be distinguishable from background such that the signal:noise ratio was sufficiently high for detection.

It has now been found that contrast agents may be used to overcome the above-mentioned problems. For example, contrast agents permit light absorption and sound generation in regions not otherwise possible. Contrast agents may also improve signal:noise ratio by increasing the amplitude of the sound wave. Increasing the sound wave amplitude allows an increase in the possible maximum depth of detection and thereby allows imaging of objects further below the surface of the body.

The use of contrast media is crucial to the success of photoacoustic imaging. Such a contrast agent for photoacoustic imaging works by either (i) enhancing the pre-existing photoacoustic effect or (ii) creating a photoacoustic effect where this was previously not possible. This may be achieved by selectively absorbing radiation in certain organs or healthy or diseased bodily structures or parts thereof, and/or by efficiently converting the radiation into heat, and/or by facilitating or improving heat-pressure conversion, and/or by scattering and diffusing the incident light so that it more uniformly illuminates the target organs.

Previously undetectable or poorly detectable objects may be identified if contrast agents are targeted to particular areas of interest. Such targeting may identify and diagnose particular disease forms, e.g. cancer, or allow detection or elucidation of particular bodily structures or organs, e.g. alimentary canal, the peripheral blood system.

Thus viewed from one aspect, the present invention provides a method of generating an image of an animate human or non-human animal body or part thereof, said method comprising administering to said body a physiologically tolerable contrast agent comprising a radiation absorbing component and/or a pressure inducing component, exposing said body to radiation, detecting pressure waves generated in said body by said radiation and generating an optoacoustic image therefrom of at least a part of said body containing the administered contrast agent.

Viewed from a further aspect, the invention provides the use of a physiologically tolerable contrast agent comprising a radiation absorbing component and/or a pressure inducing component for the manufacture of a contrast medium for administration to an animate human or non-human animal body in a method of treatment or diagnosis of said animal or part thereof, which method involves generating a photoacoustic image of said body.

This method represents a superior imaging technique over pure optical imaging of the body which is severely impeded by light scattering, even when near infrared light with a wavelength between 600 and 1300 nm is used to minimize the absorption of light by naturally occurring substances within the body. The photoacoustic effect provides the same advantages for imaging that it provides for spectroscopy: the method is still sensitive to the optical properties of the sample, but the detection method is insensitive to light scattering. In fact, light scattering can provide the beneficial effect of bathing the internal organs in approximately isotropic illumination.

Selectivity may be obtained by targeting the contrast agent to a particular organ/structure by incorporation of a targeting component or by appropriate delivery by choice of the route of administration.

Administration may be parenteral (e.g. intravenously, intraarterially, intramuscularly, interstitially, subcutaneously, transdermally, or intrasternally) or into an externally voiding body cavity (e.g the gastrointestinal tract, bladder, uterus, vagina, nose, ears or lungs), in an animate human or non-human (e.g. mammalian, reptilian or avian) body.

The methods and uses described herein are especially useful for imaging liquid- or air-filled organs or blood-containing structures, e.g. tumours, diseased tissue or particular organs, by the use of contrast agents with specificity for that region/structure, e.g. by use of biological recognition agents with the desired specificity.

"Radiation" as described herein may be electromagnetic radiation of any wavelength or frequency. Preferably, electromagnetic radiation will fall in the near-infrared region and have a wavelength in the range 600 to 1300 nm. More preferably, electromagnetic radiation will have a wavelength between 625 and 1200 nm. Most preferably it will have a wavelength in the range 650 to 1000 nm. Alternatively, electromagnetic radiation may fall in the X-ray or gamma ray region of the electromagnetic spectrum and have a wavelength less than 0.1 $\mu$m, or it may fall in the microwave region and have a frequency between 0.3 and 30 GHz.

As mentioned previously, continuous wave radiation may be used with its amplitude or frequency modulated. When continuous wave radiation is used, the photoacoustic effects may be analysed in the frequency domain by measuring amplitude and phase of one or several Fourier components. Alternatively, and preferably, short pulses (impulses) of radiation are employed which allow stress confinement. Pulses with a duration of $\leq 1$ $\mu$sec, e.g. nsec, are preferred. When pulses are used, analysis may be made in the time domain, i.e. on the basis of the time taken for the sound wave to reach the detector, thus simplifying analysis and aiding depth profiling.

As used herein, a "radiation absorbing component" is a chemical compound, complex or structure which absorbs radiation of the relevant wavelength and efficiently turns this radiation into heat.

A dye compound may form the radiation absorbing component or may be a part thereof. A dye compound or composition is a substance that absorbs electromagnetic radiation with a wavelength of 300 to 1300 nm, generally with a change in the populations of the electronic energy levels of the substance. A dye compound will be especially useful when the incident radiation is electromagnetic radiation in the near infrared region with a wavelength between 600 and 1300 nm. Understanding the molecular requirement for a dye to be used in this component requires an appreciation of the processes involved during and after the absorption of radiation.

Most molecules have a singlet ground electronic state. Absorption of a photon of radiation first raises a molecule into an excited singlet state. Generally, this will also be in an excited vibrational state. For dyes in the solid state there may also be unfavourable intermolecular interactions. For molecules in solution, there may be an unfavourable arrangement of the solvent molecules about the excited dye. Rapid rearrangement of the dye molecule itself and the molecules about it following the radiation absorption produces a molecule in an excited electronic state and ground vibrational state. A small amount of heat is released.

The molecule can then follow one of several courses. It can non-radiatively return to the ground state with the production of a relatively large amount of heat through the process of internal conversion. It can radiatively return to the ground state with the production of a photon of radiation through the process of fluorescence. Finally, it can convert into a long-lived excited triplet state through the process of intersystem crossing. Transitions from the excited triplet state to the ground state are symmetry forbidden, and the triplet state is much longer lived than the excited singlet state. Nevertheless, eventual return to the ground state with the release of a photon of radiation is possible through the process of phosphorescence.

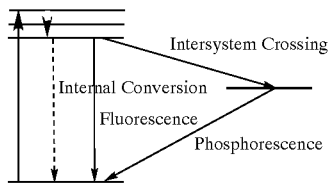

Efficient production of heat, as is generally required for the photoacoustic effect, requires that processes that compete with internal conversion are minimized. Thus, preferably, a dye to be used in the radiation absorbing component will weakly fluoresce and weakly phosphoresce. Fortunately phosphorescence and fluorescence are inherently weak for many dyes absorbing wavelengths of light in the range 600–1300 nm, the preferred range for which absorbance by naturally occurring substances of the body is low.

Alternatively, the contrast agent may take up X-rays or gamma rays with the generation of heat. The molecular requirements for such an agent are somewhat different from those for an agent that absorbs near-infrared light. Generally, any element with an atomic number greater than 20 is capable of absorbing X-rays, depending upon the X-ray source and the wavelength or K-edge of the element. Even gases like xenon are known to absorb X-rays and have been used for X-ray diagnostic imaging by CT of the brain and other tissues within the body. An appropriately chosen X-ray photon carries sufficient energy to release electrons from the atoms making up the contrast agent. Energy transfer from those electrons to lattice vibrations then produces heat. Thus, a contrast agent for photoacoustic imaging with X-rays should have electrons that are readily ionized by X-rays.

One aspect of the invention is the use of iodinated aromatic compounds, such as those already widely used to enhance contrast in X-ray images, as contrast agents for photoacoustic imaging. The number of iodine atoms per molecule can range from 1 to 6 (e.g. as in "dimer" contrast agents like iodixanol, iodipamide, etc.), with a greater number of iodine atoms providing an enhanced signal. Polymeric contrast agents with many iodine atoms per molecule would be the logical extension of such contrast agent preparation. These would include both conventional branched and linear polymers as well as dendrimeric materials. These same materials will be particularly suitable for photoacoustic X-ray imaging when therapeutic doses of the X-rays or gamma rays are employed, since it is known that with high X-ray doses these compounds release electrons (see R. S. Mello, H. Callisen, J. Winter, R. Kagan and A. Norman, "Radiation dose enhancement in tumors with iodine", *Med. Phys.* 1983, 10, 75; and K. S. Iwamoto, A. Norman, A. R. Kagan, M. Wollin, A. Olch, Imgram M. Bellotti and R. G. Skillen, "The CT scanner as a therapy machine", *Radiother. Oncol.* 1990, 19, 337). Because electron production can potentially lead to cell damage, photoacoustic imaging with X-rays may be most useful in conjunction with radiation therapy.

More generally, any compound containing heavy atoms, especially iodine, tungsten or barium, will be useful as a contrast agent for photoacoustic imaging with X-rays. These may be soluble liquids or solids or may be suspensions of solid particles in a physiologically acceptable liquid. Alternatively they may be solid or liquid materials encapsulated into liposomes.

Alternatively, the contrast agent may absorb microwaves and generate heat. When microwaves penetrate a solid, liquid or gas, the oscillating electric fields of the radiation induce periodic translational motion in charged particles and ions and periodic rotational motion in dipolar species. The translational and rotational motions are opposed by frequency-dependent inertial, elastic and frictional forces, and heat is built up with accompanying dissipation of the oscillating electric field. When the substance contains species with a net magnetic moment, such as magnetite particles, the interaction of those particles with the oscillating magnetic field of the radiation also leads to the generation of heat.

The efficiency with which a given substance converts microwaves into heat is measured generally by the dielectric loss factor at the microwave frequency. Any substance with a high loss factor at the microwave frequency, preferably with a loss factor higher than that of water, is potentially useful as a contrast agent for photoacoustic imaging with microwaves.

Another aspect of the invention is the use of suspensions of superparamagnetic particles as contrast agents for photoacoustic imaging. Still another aspect of the invention is the use of suspended particles of certain ceramics, especially $Co_2O_3$, $MnO_2$, NiO and CuO, as contrast agents for photoacoustic imaging with microwaves.

Radiation absorbing components of the invention may consist of solid particles, liquid solutions, solids that go into solution upon introduction into the body or gas bubbles, or a combination of two or more of the different phases, where the components of the different phases may be chemically the same or different. For the sake of clarity, the word "particle" is used to refer to any physiologically acceptable particulate material. Such particles may be solid (e.g. coated or uncoated crystalline materials) or fluid (e.g. liquid particles in an emulsion) or may be aggregates (e.g. fluid-containing liposomes). When particulate matter is used this may scatter radiation so that it is more uniformly distributed within the target organs and has an enhanced probability of being absorbed as a result of the increased mean path length followed by frequently scattered photons.

"Gas", "liquid" and "solid" as used herein refer to the physical state of the contrast agent or of its one or several components at the normal body temperature of the animal to which the contrast agent is to be administered, e.g. 37° C. for humans.

A "pressure inducing component" is a compound, complex or structure which on heating or on irradiation at the relevant wavelength induces pressure in its immediate environs which would be detectable as a sound wave. Preferably, the pressure inducing component is thermally expandable and expands when heated by the heat released from a radiation absorbing component (which may be naturally occurring), sufficiently to produce a pressure wave which would be detectable. Such a pressure inducing component may consist of solids, liquids or preferably a gas, for example in the form of bubbles, or a mixture thereof, in which the solid, liquid or gas molecules may be the same or different. The pressure inducing component may also comprise emulsion droplets. Included within the scope of such components are agents which generate pressure through the initiation of chemical reactions. Thus, components used in the invention include precursors, i.e. compounds, complexes or structures which on irradiation or heating (as described above) produce a pressure inducing component such as a thermally expandable component or molecules which occupy a greater volume. An example of such a precursor is graphite which on heating with water, or as a result of radiation absorption, produces CO and $H_2$, both of which are thermally expandable. This thus produces both an increase in volume due to the production of gases and further expansion due to heating of these gases, thus resulting in a pressure wave. Other examples of gas precursors include aminomalonate, carbonates and bicarbonates, physiologically acceptable diazonium compounds, carbonate esters containing groupings of the type —CO—O—$CR^1R^2$—O—CO—$OR^3$, and β-ketoacids. These may react in a variety of ways to generate gas. Thus, for example, in the presence of photochemical reactions that generate $H^+$ ions, carbonates and bicarbonates may generate carbon dioxide in vivo following administration; diazonium compounds may generate nitrogen on irradiation if UV light is used; carbonate esters liberated by photochemical reactions will interact with non-specific esterase in vivo, leading to elimination of carbon dioxide; and β-ketoacids will decarboxylate. The pressure inducing component may be consumed during the course of the above described chemical reaction producing a pressure-wave, or may simply act as a catalyst.

It will be appreciated that radiation absorbing components which efficiently convert radiation into heat will inherently have pressure inducing properties (if the local environment is already susceptible to a pressure change on heating). However, a pressure inducing component may additionally (or alternatively) be added which aids or allows conversion of heat generated into pressure (or converts radiation directly into pressure through chemical reaction). Similarly it will be appreciated that a pressure inducing component may also inherently have radiation absorbing features, e.g. gases which absorb radiation of the relevant wavelength, or graphite which absorbs radiation and may produce gas as a pressure inducing component. Thus, in some cases the same physical entity (e.g. a compound or complex) or physical state (e.g. gas) may have both a radiation absorbing component and a pressure inducing component.

If both a radiation absorbing component and a pressure inducing, preferably thermally expandable, component are used, these may be administered separately, simultaneously or sequentially. Optionally, they may be contained in the same compound, complex or structure. For example, gas bubbles or microballoons may be produced in which the gas is surrounded by a membrane containing or consisting of a suitable radiation absorbing component such that heat resulting from radiation absorption may readily be transferred to the gas. A kit of parts suitable for separate, simultaneous or sequential administration of components of contrast agents for use according to the invention, forms a further aspect of the invention.

The contrast agent which comprises a radiation absorbing component and/or a pressure inducing component (which themselves may be composed of different phases and different molecules within those phases, wherein the molecules are referred to herein as the "elements" of each component), may, as a whole, consist of solid particles, emulsion droplets, solids that go into solution upon introduction into the body, liquid solutions or gas or a combination of two or more of these.

Optionally the absorption wavelengths or other optical properties of one or more elements of the contrast agent may be sensitive to the biochemical or biophysical properties of the organs in which they are or become contained or located. For example, the absorption wavelengths of elements of the radiation absorbing component, such as dyes, may be sensitive to local pH.

Solid contrast agents may comprise a light-absorbing dye or they may comprise a core of a colourless material, e.g. a gas, and a shell composed of a light-absorbing dye. Alternatively they may comprise substances that absorb X-rays or microwaves, or they may comprise a core of non-absorbing substance and a shell of a substance that absorbs X-rays or microwaves. Preferably the dye will absorb in the wavelength range 300–1300 nm, more preferably in the wavelength range 600–1300 nm.

Generally, solid contrast agents should be formulated as particles with diameter sizes between 5 and 10000 nm, preferably between 10 and 2000 nm suspended in aqueous solution. Preferably, to ensure optimal absorption of light (other than microwave radiation) and particle heating, the particles should have diameters of 100 to 500 nm. However, superparamagnetic particles for absorption of microwaves will preferably have diameters of 5 to 30 nm, more preferably 5 to 20 nm, most preferably 5 to 15 nm. Such particles may be composed exclusively of the radiation absorbing components and/or the pressure inducing component or may also include other components which may be evenly or inhomogeneously distributed through the particles such as in a multicompartment structure, or may, for example, form a central core or domain to which components of the contrast agent are attached, or vice versa.

Preferably solid particles are coated or can be mixed at up to 100% by weight of particle with a surfactant to impede aggregation during autoclaving and storage.

In one aspect, a preferred physiologically tolerable contrast agent of this invention comprises at least one chromophoric group attached to a surfactant molecule.

In this invention, a surfactant molecule is defined as an emulsifier or detergent as listed in McCutcheon's Directories, Volume 1: Emulsifiers and Detergents (1994), and which contains at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

Chemical functional groups in the surfactant molecules can be interconverted by chemical reactions well known to those skilled in the art. For example, a hydroxyl group can be converted to a methanesulfonic acid ester which can be treated with sodium azide and reduced to form an amine group. Carboxylic acid groups and ketones can be reduced to form alcohols, and alcohols can be oxidized to form ketones, aldehydes, and carboxylic acid groups.

Useful surfactant molecules are emulsifiers or detergents which can function as dispersing agents, wetting agents, adsorbents, anticaking agents, soil antiredispositioning agents, antistats, binders, carriers, pearlescents, conditioning agents, hydrotropes, defoamers, emollients, flocculants, humectants, lubricants, opacifiers, plasticizers, preservatives, release agents, scale inhibitors, stabilizers, suspending agents, thickeners, UV absorbers, water repellants, waxes, and polishes, and which contain at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, a phosphonic acid group, a phenolic group, a sulfonic acid group, a carbon-carbon double bond, and a ketone.

Preferably, the surfactant molecule comprises a polyalkyleneoxide moiety, optionally containing a branching group as defined herein; more preferably a polyalkyleneoxide block copolymeric moiety, optionally containing a branching group as defined herein; and most preferably a polyalkyleneoxide block copolymeric moiety optionally containing a branching group as defined herein and comprising a polypropylene oxide block and a polyethyleneoxide block. Examples of useful surfactant molecules include block copolymers such as AL 2070 available from ICI Surfactants, Antarox block copolymers available from Rhone-Poulenc, Delonic block copolymers available from DeForest, Inc., Hartopol block copolymers available from Texaco Chemical Canada, Macol block copolymers available from PPG Industries, Marlox block copolymers available from Huls America, Pluronic block copolymers including Pluronic F, L, P and R available from BASF Corp., Poly-Tergent block copolymers available from Olin Corp., and Tetronic and Tetronic R block copolymers available from BASF Corp. Currently preferred surfactant molecules include Tetronic and Pluronic block copolymers, and currently most preferred are Tetronic block copolymers.

When the agents are intended for injection into the vascular system, they may be coated or be mixed at up to 100% by weight of particle with a polymer-containing substance such as poly(ethylene glycol) to slow clearance from the bloodstream. Optionally, the solution in which solid particles are suspended may contain buffers and other excipients to control the pH and osmolality.

When contrast agents containing liquid radiation-absorbing elements are used, these may be solutions of stabilized dyes or solutions of highly soluble dyes that are formulated in advance or that are prepared immediately before use. Preferably the dyes are chosen for optimum efficiency in the conversion of absorbed radiation into heat according to the principles described above and will have a maximum in absorbency of light between wavelengths of 300 and 1300 nm, more preferably between wavelengths of 600 and 1300 nm. The dyes may be incorporated into a polymer such as a branched or linear polymer containing poly(ethylene glycol) and may have groups such as hydroxyl-containing alkyl groups or sulfonate attached to enhance their stability or solubility in water. Suitable materials are disclosed in International Patent publications Nos. WO 96/17628 (Schering) and WO 96/23522 (Daiichi), the contents of which are incorporated herein by reference.

Generally, lipophilic contrast agents are formulated as oil-in-water emulsions with oil droplet sizes between 5 and 10000 nm, preferably between 10 and 2000 nm, suspended in a pharmaceutically acceptable aqueous phase. Preferably, to ensure optimal light absorption and particle heating, the droplets should have diameters of 50 to 500 nm. Such oil droplets may be composed exclusively of the radiation absorbing component(s) or may include other lipophilic substances distributed throughout the droplet. The droplet itself is the "pressure inducing component" of the contrast agent whereby the pressure wave required for acoustic detection is initiated at the interface between the oil and water phases. These emulsions will likely contain pharmaceutically acceptable excipients as known in the art including lecithin, other phospholipids, surfactants such as the Tetronics and Pluronics, lipophilic additives such as sesame oil, and conventionally used components for isotonicity, pH and osmolality control.

When soluble dyes are to be supplied in aqueous solutions, the solutions optionally may contain stabilizing agents as taught in WO94/23646, incorporated herein by reference. The solutions may also contain excipients to control the pH or osmolality.

Soluble dyes may optionally be enclosed in micelles or liposomes as taught in WO96/23424 incorporated herein by reference. Liposomal formulations may optionally contain substances to stabilize the dyes against oxidation or other degradative processes.

Alternatively the contrast agents may contain soluble compounds comprising heavy atoms such as iodine. Solutions of iodinated compounds may be formulated in advance or may be prepared immediately before use. Preferably the iodinated compounds are chosen for optimum efficiency in the conversion of absorbed X-rays and gamma rays into heat according to the principles described above and will have a maximum in absorbency of X-rays and gamma rays with a wavelength less than 1.0 $\mu$m. The iodinated compounds may be incorporated into a polymer such as a linear polymer containing poly(ethylene glycol) and may have groups attached to enhance their solubility in water. When iodinated compounds are to be supplied in aqueous solutions, the solutions optionally may contain excipients to control the pH or osmolality. Suitable iodinated compounds may optionally be enclosed in micelles or liposomes.

When a gas forms an element of a contrast agent, the contrast agent is preferably in the form of a gas-containing structure, e.g. a vesicle (e.g. liposome, micelle,- microballoon, etc.), or the gas is in one or more compartments of a multi-compartment structure. Such gas-containing structures are preferably 1000–6000 nm in diameter. Such gas-containing structures can be similar or identical to those used as contrast agents for ultrasonic imaging. The preparation of gas-filled microparticles or microballoons for use in ultrasonic imaging is described in WO95/06518 which is incorporated herein by reference.

Preferably, to additionally provide a radiation-absorbing component for photoacoustic imaging, either the gas itself or at least one component of the enclosing shell should strongly absorb radiation, which preferably will have a wavelength of between 300 and 1300 nm, more preferably between 600 and 1300 nm. This may be achieved by the use of one or more dye or dye-containing compounds which absorb radiation at the appropriate wavelength, as a component of the enclosing shell.

Suitable gases, or mixtures thereof, include common blood gases $CO_2$, $O_2$, $N_2$, although preferably gases occurring in biological tissues should be avoided to improve the signal:noise ratio. The gas may be mixed with a noble gas, as a diluent, such as argon, helium, neon or xenon which will maximize energy transfer to translational energy of the absorbing gas being diluted as these gases have no internal (rotational and vibrational) degrees of freedom (see Putterman, February 1995, Scientific American, p32–37, concerning the effect of noble gases on the photoacoustic effect).

When the contrast agent is a gas- or liquid-containing structure, the stability of the surrounding shell may be sufficiently low such that heating as a consequence of irradiation results in disruption of the structure and release of the contents. This may itself generate a pressure wave, producing a signature effect for the contrast agent, and/or may be used to simultaneously release required molecules into the local environs, e.g. therapeutically active compounds.

To obtain selectivity, the contrast agent may be passively or actively targeted to regions of diagnostic interest such as organs, vessels, sites of disease, tumorous tissue, or a specific organism in a patient. In active targeting, the contrast agents may be attached to biological recognition agents to allow them to accumulate in or to be selectively retained by or to be slowly eliminated from certain parts of the body, such as specific organs, parts of organs, bodily structures and disease structures and lesions. The recognition agents may be attached to elements of the radiation absorbing and pressure inducing components or may be attached to other components of the contrast agents, such as structural components which might be used, for example in the production of contrast agent particles or microballoons. Active targeting is defined as a modification of biodistribution using chemical groups that will associate with species present in the desired tissue or organism to effectively decrease the rate of loss of contrast agent from the specific tissue or organism.

Active targeting of a contrast agent can be considered as localization through modification of biodistribution of the contrast agent by means of a targeting chemical group or ligand that is attached to or incorporated into the contrast agent. The ligand or targeting group can associate or bind with one or more receptor species present in the tissue or organism of diagnostic interest. This binding will effectively decrease the rate of loss of contrast agent from the specific tissue or organism of diagnostic interest. In such cases, the contrast agent can be modified synthetically to incorporate the targeting ligand or targeting vector. Targeted contrast agents can localize because of binding between the ligand and the targeted receptor. Alternatively, contrast agents can distribute by passive biodistribution, i.e., by passive targeting, into diseased tissues of interest such as tumors. Thus, even without synthetic manipulation to incorporate a targeting ligand or vector that can bind to a receptor site, passively targeted contrast agents can accumulate in a diseased tissue or in specific locations in the patient such as the liver. The present invention comprises use of a contrast agent that is linked to a targeting vector (also referred to as a ligand) that has an affinity for binding to a receptor. Preferably the receptor is located on the surface of a diseased or disease-causing cell in a human or animal patient.

In one aspect, the receptor comprises a dihydrofolate reductase enzyme (also referred to as a DHFR receptor). DHFR receptors are present in certain disease causing bacteria and are expressed in relatively large numbers on certain tumor cells. Suitable ligands that can bind to these DHFR receptors include folic acid and folic acid derivatives including 7,8-dihydrofolate derivatives, antifolate drugs, DHFR antagonists and agonists and inhibitors, trimethoprim and trimethoprim analogs which can bind to DHFR sites in bacteria, methotrexate and methotrexate analogs which can bind to DHFR sites on tumor cells, pyrimethamine, and tetroxoprim. Descriptions of suitable ligands that can bind to DHFR receptors are outlined in WO 9413327 which is incorporated herein by reference. Ligands that are most preferred comprise derivatives of the antifolate drugs, methotrexate and trimethoprim.

In one aspect, contrast agents useful in this invention are radiation absorbing and pressure inducing components which comprise ligands such as derivatives of trimethoprim and methotrexate that are chemically linked to chromophores or dyes to form targeted ligand-dye conjugates. Preferred dyes absorb in the region from 300 to 1300, and more preferably from 600 to 1300 such as cyanine dyes. One or more ligands can be linked to one or more dyes, for example, by use of a peptide as a linking group between the dye and the ligand. Useful trimethoprim and methotrexate derivatives that comprise a reactive primary amine group are described in WO 94/13327. Such primary amine derivatives can react with dyes that contain reactive functional groups such as, for example, isothiocyanate (NCS) groups (and thus useful cyanine dyes can be described herein as DYE-NCS and are further outlined below), cyanate groups, vinyl chloride groups, active ester groups such as N-hydroxysuccinimide (NHS) groups, and nitrophenyl ester groups. Representative non-limiting examples of cyanine dyes that contain useful reactive functional groups include, for example, CY™ dyes available from Amersham Inc., dyes disclosed in European Patent Application 0 670 374 A1, and dyes disclosed by N. Narayanan and G. Patonay in Journal of Organic chemistry (1995), 60, 2391–2395. Examples of the preparation of radiation absorbing and pressure inducing components useful in this invention that can actively target DHFR receptors are outlined in Schemes 1 and 2 below. The schemes use isothiocyanate linking chemistry as a non-limiting example.

Scheme 1.
Trimethoprim-dye derivatives useful in this invention can be prepared as follows:
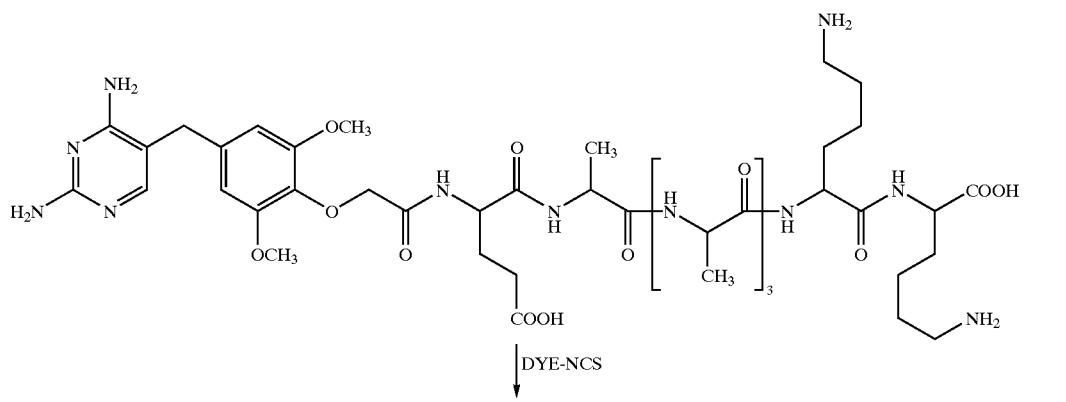
Scheme 2.
Methotrexate-dye derivatives useful in this invention can be prepared as follows:
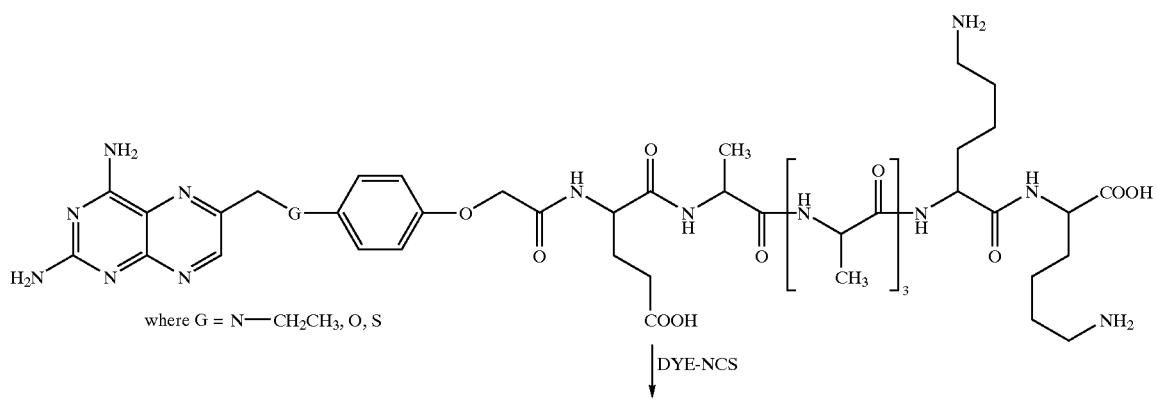

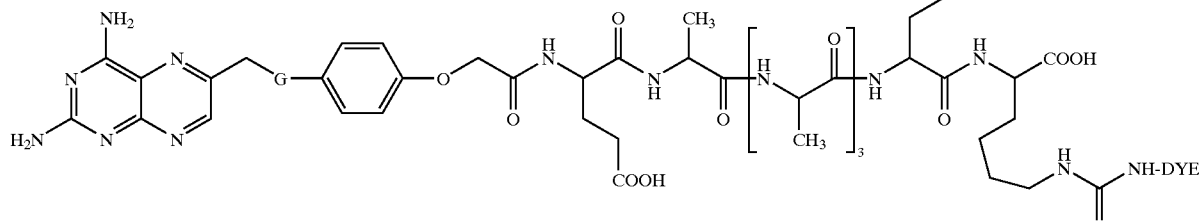

An example of a useful reactive dye (DYE-NCS) in the above scheme is:

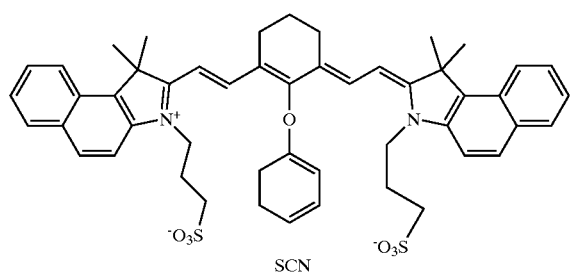

An example of a useful reactive dye which employs active ester chemistry (DYE-NHS, where NHS refers to N-hydroxysuccinimide) instead of isothiocyanate chemistry (DYE-NCS) to form targeted ligand-dye conjugates through an amide (—NH—C(=O)-DYE) bond instead of through a thiourea bond (NH—C(=S)—NH-DYE) in schemes 1 and 2, above, is Amersham Incorporated's Cy5™ reactive dye:

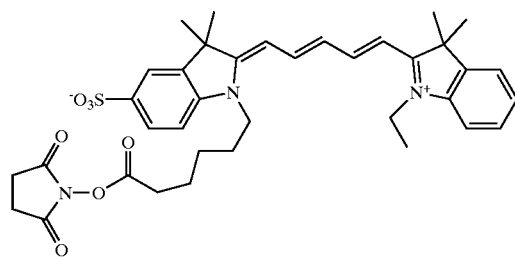

The number of radiation absorbing and pressure inducing dyes attached to the ligand which targets the DHFR receptor can vary from one to about 100, preferably from one to about 10, and more preferably from one to about 3. Variations in the number of dyes attached to the DHFR ligands in Schemes 1 and 2 can be accomplished. by changing the number of lysine groups synthetically incorporated into the peptides shown in Schemes 1 and 2, and then treating with enough reactive dye to react with each lysine amine.

Targeted ligand-dye conjugates thus produced can be formulated in a pharmaceutically acceptable medium such as, for example, in sterile phosphate buffered saline solution, and then administered to a patient by, for example, intravenous injection.

Ligands in these targeted ligand-dye conjugate contrast agents will bind to DHFR receptors such as, for example, to DHFR receptors in bacteria associated with an infection in the patient in the case of a trimethoprim targeted ligand-dye conjugate derivative, and to DHFR receptors in cancerous cells in the case of a methotrexate targeted ligand-dye conjugate derivative. Contrast agent that does not bind to a DHFR receptor will be cleared from the patient at a faster rate than receptor bound contrast agent through commonly available drug elimination mechanisms such as via the liver or kidney while contrast agent that binds to DHFR receptors in areas of disease in the patient will remain associated with those areas of disease for a prolonged time with respect to the amount of unbound ligand-dye conjugate. When the patient or a portion of the patient is then subjected to a photoacoustic imaging procedure after an amount of non-receptor bound contrast agent has been allowed to clear from the patient, areas of enhanced signal intensity will derive from sites where contrast agent is bound, i.e. from sites containing DHFR receptor to which the targeted ligand-dye radiation absorbing and pressure inducing conjugate is bound.

Other methods of attachment of suitable dyes to ligands are readily apparent to one skilled in the art.

The use of biological recognition agents (or "vectors") for targeting contrast agents has been described in detail in U.S. patent application Ser. No. 08/848,586 entitled "Method of tumor treatment" filed on Apr. 29, 1997 in the name of William Anthony Sanderson, and in International Patent Application No. PCT/GB98/01245, both of which are incorporated herein by reference. Appropriate biological recognition agents include amino acids, peptides, antigens, haptens, enzyme substrates, enzyme cofactors, enzyme inhibitors, biotin, hormones, neurohormones, neurotransmitters, growth factors, lymphokines, lectins, toxins, carbohydrates, oligosaccharides, polysaccharides, dextrans, oligonucleotides stabilized against nucleases, receptor-binding drugs and ligands, antibodies, and functional fragments thereof. It will be appreciated that the appropriate choice of a biological recognition agent will depend on the organ to be targeted and the route of administration, but will generally rely on binding to one or more surfaces of body organs, structures, or biological organisms, especially to the cells of these surfaces which may uniquely be recognized by the presence of unique surface characteristics, e.g. number or type of receptor, or antigen expression.

Appropriate dyes and dye-containing molecules such as polyethylene glycol derivatives of dyes for use in contrast agents used in the invention, particularly for the preparation of contrast agents in which are used non-solid particles having a shell comprising a dye, which shell surrounds gas molecules, should have an absorption maximum in the range of 300 to 1300 nm, more preferably 600 to 1300 nm. Dyes for use in the invention include compounds having an extensive delocalized electron system, e.g. cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, naphthoquinones, indathrenes, phthaloylacridones, trisphenoquinones, azo dyes, intramolecular and intermolecular charge-transfer dyes and dye complexes, tropones, tetrazines, bis (dithiolene) complexes, bis(benzene-dithiolate) complexes, iodoaniline dyes, bis(S,O-dithiolene) complexes, etc. Examples of suitable organic or metallated dye compounds may be found in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals" Haugland, Molecular Probes Inc, 1996, DE-A-4445065, DE-A-4326466, JP-A-3/228046, Narayanan et al. J. Org. Chem. 60: 2391–2395 (1995), Lipowska et al. Heterocyclic Comm. 1: 427–430 (1995), Fabian et al. Chem. Rev. 92: 1197 (1992), W096/23525, Strekowska et al. J. Org. Chem. 57: 4578–4580 (1992) and W096/17628.

Unless otherwise specified, an alkyl group as defined herein may be linear or branched, saturated or unsaturated, may contain an ether oxygen group, and may contain one or more rings comprising 3 to 6 carbon atoms such as cyclopropyl, spirocyclopropyl, cyclopropylidene, cyclobutyl, spiro-1,1-cyclobutyl, 1,2-cyclobutylidene, 1,3-cyclobutylidene, cyclopentyl, 1,2-cyclopentylidene, cyclopenten-3-yl, cyclohexyl, 1,4-cyclohexylidene, 2,3-bicyclo[2.2.1]heptylidene, 1-decalin, phenyl, 1,4-phenylene, and the like, and may be substituted with one or more substituents selected from the group consisting hydroxyl, 1,2-dihydroxyethyl, 1,2-dihydroxy-propyloxy, carboxyl, sulfonate, phosphonate, and poly(alkylene oxidyl) such as ω-hydroxypoly(ethylene oxidyl) and ω-methoxypoly(ethylene oxidyl) the molecular weights of which can be up to about 50,000.

Preferably dyes of formula I may be used:

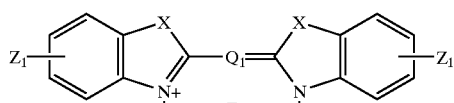

(I)

wherein
each $Z_1$ is independently selected from the group consisting of:
hydrogen,
a methyl group optionally substituted with a substituent selected from the group consisting of hydroxyl, carboxyl, sulfonate, phosphonate, and poly(alkylene oxidyl) such as ω-hydroxypoly(ethylene oxidyl) and ω-methoxypoly(echylenie oxidyl) the molecular weights of which can be up to about 50,000,
an ethyl group optionally substituted with one or two substituents selected from the group consisting of hydroxyl, carboxyl, sulfonate, phosphonate, and poly(alkylene oxidyl) such as ω-hydroxypoly(ethylene oxidyl) and ω-methoxypoly(ethylene oxidyl) the molecular weights of which can be up to about 50,000,
an ethylene group optionally substituted with one or two substituents selected from the group consisting of hydroxyl, carboxyl, sulfonate, phosphonate, and poly(alkylene oxidyl) such as ω-hydroxypoly(ethylene oxidyl) and ω-methoxypoly(ethylene oxidyl) the molecular weights of which can be up to about 50,000,
a $C_{3-16}$ alkyl group, the alkyl portion of which is optionally substituted as defined above,
a $C_{1-16}$ alkoxyl ether group, the alkyl portion of which is optionally substituted as defined above,
a $C_{1-16}$ carboxyalkyl ester group, the alkyl portion of which is optionally substituted as defined above,
a $C_{1-16}$ oxycarbonylalkyl ester group, the alkyl portion of which is optionally substituted as defined above,
a $C_{1-16}$ carbonylaminoalkyl amide group, the alkyl portion of which is optionally substituted as defined above,
a $C_{1-16}$ aminocarbonylalkyl amide group, the alkyl portion of which is optionally substituted as defined above,
a carboxylic acid group which may be a carboxylate group,
a sulfonate group,
a hydroxyl group,
a phosphate group,
a $C_{1-16}$ sulfonamidoalkyl group, the alkyl portion of which is optionally substituted as defined above,
a $C_{1-16}$ aminosulfonylalkyl group, the alkyl portion of which is optionally substituted as defined above,
a $C_{1-16}$ aminocarbonylaminoalkyl urea group, the alkyl portion of which is optionally substituted as defined above,
a $C_{1-16}$ aminothiocarbonylaminoalkyl thiourea group, the alkyl portion of which is optionally substituted as defined above,
a phenyl-$C_{1-16}$-alkyl group, the alkyl portion of which is optionally substituted as defined above,
a phenoxy-$C_{1-16}$-alkyl group, the alkyl portion of which is optionally substituted as defined above,
a $C_{1-16}$ phenyloxyalkyl group, the alkyl portion of which is as defined above,
an oxyphenoxy-$C_{1-16}$-alkyl group, the alkyl portion of which is optionally substituted as defined above,
a poly(alkylene oxidyl) group such as hydroxypoly (ethylene oxidyl) and methoxypoly(ethylene oxidyl) with a molecular weight up to about 50,000,
and an annulated aromatic ring which comprises a benz[e]aromatic ring, a benz[f]aromatic ring, or a benz[g]aromatic ring, where e, f, and g are defined relative to the indole structure as a template and each of which ring may be substituted by $C_{1-16}$ alkyl, $C_{1-16}$ alkoxyl, carboxyl, sulfonate, sulfonamido, phenyl, poly(alkylene oxidyl) or phenoxyl groups as defined above;
each $R_1'$ is independently selected from the group consisting of methyl and a $C_{2-16}$ alkyl group including a substituted alkyl group where alkyl is optionally substituted as defined above,
each X is independently selected from the group consisting of O, N—$R_1'$, S, Se, Te, CH=CH, and $(CH_3)_2C$; and
$Q_1$ is selected from the group consisting of:
$(CH=CH)_n$ where n has a value of 1 to 6,

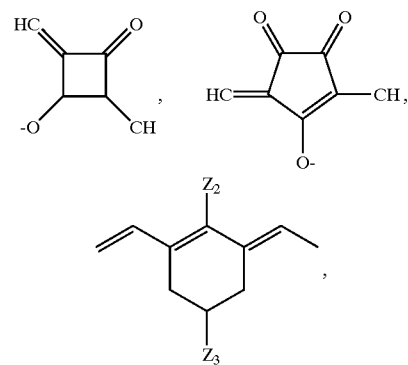

where $Z_2$ is selected from the group consisting of H, chloro, O-alkyl, S-alkyl, where alkyl is optionally substituted as defined above, O-poly(alkylene oxidyl), S-poly(alkylene oxidyl), where poly(alkylene oxidyl) is as defined above and also includes poly(alkylene oxide) groups to which another dye is attached at the ω-end, O-phenyl, S-phenyl, wherein the phenyl groups may be substituted with alkyl groups optionally substituted as defined above, O-alkyl groups as defined above, S-alkyl groups as defined above, aminothiocarbonylaminoalkyl groups, and aminothiocarbonylaminophenyl groups, and where $Z_3$ is selected from the group consisting of H, carboxylate, and carboxyalkyl where alkyl is as defined above, carbonylaminoalkyl where alkyl is as defined above, and carbonylaminophenyl where phenyl is as defined above, and and 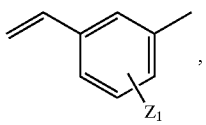

$Z^-$ is a physiologically tolerable counterion, preferably I, Br, Cl, or OAc.

More preferably dyes of formula II may be used:

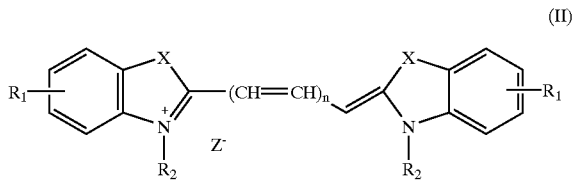

(II)

wherein n is an integer having a value of 1 to 6;

each $R_1$, which may be the same or different, represents a hydrogen atom or a solubilizing group, or adjacent $R_1$ substituents together with the ring carbons to which they are attached may form a ring structure, preferably a 5- or 6-membered ring, for example an aromatic ring;

each $R_2$, which may be the same or different, represents a hydrogen atom or a lipophilic group, e.g. an optionally unsaturated $C_{1-24}$ alkyl group, preferably a $C_{6-18}$ group, especially when the dye is to be used as part of a gas-containing non-solid particle, alternatively, each $R_2$ may be an optionally unsaturated $C_{2-8}$ alkyl group which is attached to one or more solubilizing groups;

each X, which may be the same or different, each represents 0, S, —CH=CH— or $C(R_3)_2$ in which each $R_3$, which may be the same or different, represents a hydrogen atom or more preferably a methyl or ethyl group;

Z is a physiologically tolerable counterion, preferably I, Br or Cl.

Examples of suitable solubilizing groups include sulfate, carboxylate, phosphate, hydroxy, oxyacid and thiol groups as well as $C_{1-6}$ alkyl groups substituted with one or more such groups.

Contrast media for use according to the invention containing the contrast agent may include other components for example conventional pharmaceutical formulation aids such as wetting agents, buffers, disintegrants, binders, fillers, flavouring agents and liquid carrier media such as sterile water, water/ethanol etc. The contrast agent should be suitable for administration either by injection or inhalation or catheterization or instillation or transdermal introduction into any of the various body cavities including the alimentary canal, the vagina, the rectum, the bladder, the ureter, the urethra, the mouth, etc.

For oral administration, the pH of the composition is preferably in the acid range, e.g. 2 to 7, and buffers or pH adjusting agents may be used.

The contrast media may be formulated in conventional pharmaceutical administration forms, such as tablets, capsules, powders, solutions, dispersion, syrups, suppositories etc.

The preferred dosage of the contrast media will vary according to a number of factors, such as the administration route, the age, weight and species of the subject, but in general containing in the order of from 1 pmol/kg to 1 mmol/kg bodyweight of the contrast agent.

Imaging of the desired area is performed by detection and appropriate analysis of the sound waves resulting from irradiation. Detection may be performed at the same surface of the sample as the source of incident radiation (reflection) or alternatively at another surface such as the surface diametrically opposed to the incident light, i.e. the sample's back surface (transmission). Suitable methods of detection include the use of a microphone, piezoelectric transducer, capacitance transducer, fiber-optic sensor or alternatively non-contact methods (see Tam, 1986, supra for a review). Techniques and equipment used in ultrasound imaging may be used.

FIG. 1a is a graph of comparative biodistribution data of contrast agent NC100448 versus indocyanine green as control in female immunodeficient mice containing HT-29 tumors at one hour post intravenous injection of phosphate buffered saline solutions of each. NC100448 is detected in the tumor; the control compound is negligibly detected.

FIG. 1b is a graph of comparative biodistribution data of contrast agent NC100448 versus indocyanine green as control in female immunodeficient mice containing HT-29 tumors at three hours post intravenous injection of phosphate buffered saline solutions of each. NC100448 is detected in the tumor; the control compound is negligibly detected. Relative to FIG. 1a, the concentration of the contrast agent in the tumor has increased while the concentration in the blood has decreased.

Figure 2:
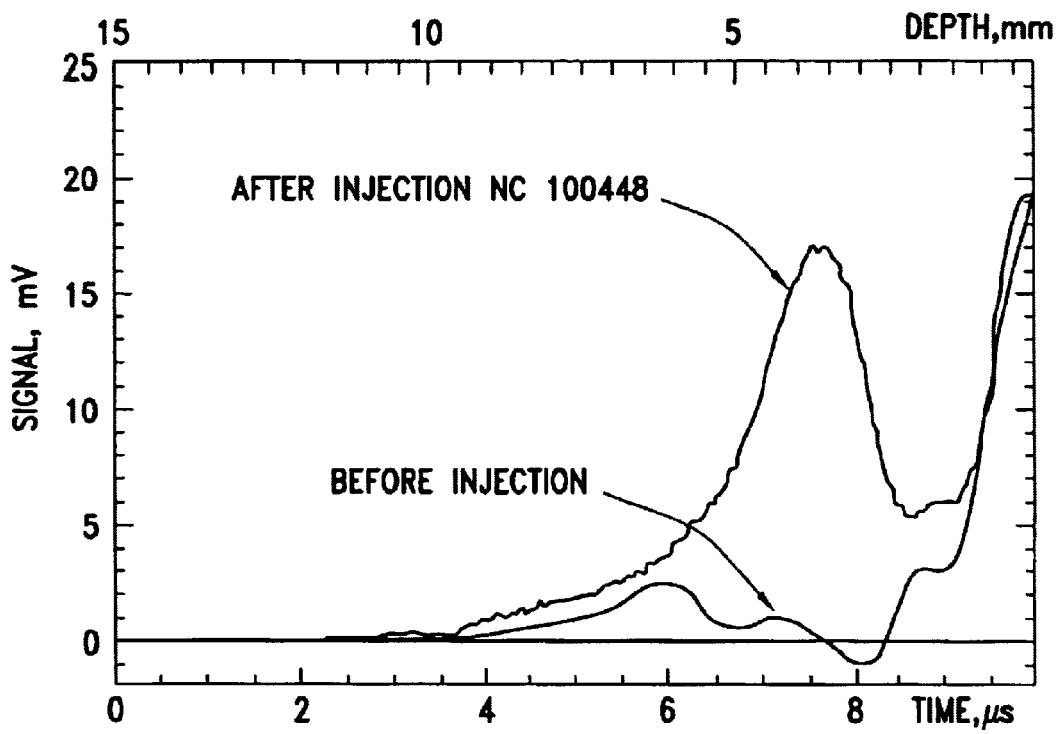
FIG. 2 shows one-dimensional images obtained from a hairless, immunocompetent mouse before and after injection of a solution of NC100448 into the tail vein (see Example 7 below).

Preferred embodiments of the invention will now be described by reference to the following non-limiting examples:

EXAMPLE 1
Suspended Dye Particulates

The poorly soluble dye 3,3'-diethythiatricarbocyanine iodide (Fisher) is added to a 1.5 oz brown glass bottle containing approximately 12 ml of 1.1 mm diameter beads of zirconium sulfate in an amount sufficient to be 15% (wt/vol) of the final suspension. The solution in the bottle is also made 3% in Pluronic F-68 and 10% in PEG-400 (Shearwater). It is milled at approximately 150 rpm for up to a total of 9 days, during which time the particle size is monitored by light scattering or other analytical methods. The process is stopped when the average particle size is 100–400 nm in diameter. The resulting product will have an absorption maximum around a wavelength of 772 nm and may be autoclaved without change in particle size.

EXAMPLE 2
Suspended Graphite Particles

Powdered graphite is processed by the method of Example 1.

EXAMPLE 3
Preparation of 2-[2-[2-(4-isothiocyano)phenoxy-3-[[1,3-dihydro-1,1-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt, Sodium Salt, Reaction Product With PEG 3400 α,ω-Diamine The following reaction scheme was used to produce the title compound:

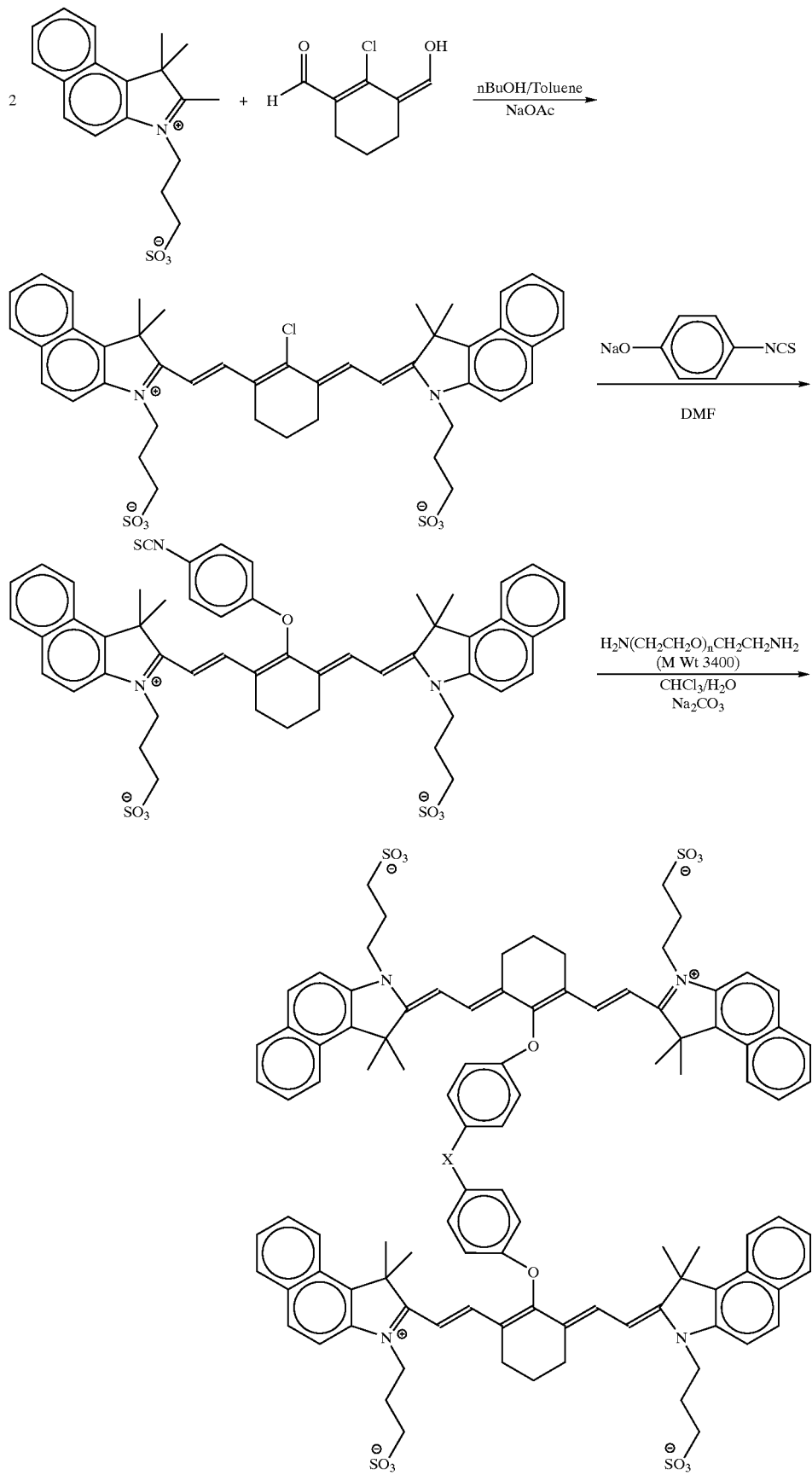

wherein X is NH-CS-NH(CH$_2$CH$_2$O)$_n$CH$_2$CH$_2$NH-CS-NH).

EXAMPLE 4

Preparation of 2-[2-[2-(4-isothiocyano)phenoxy-3-[[1,3-dihydro-1,1-dimethyl-3-(3-Bulfopropyl)-2H-benz[e]indol-2-ylidene]ethylidene]-1-cyclohexen-1-yl]ethenyl ]-1,1-dimethyl-3-(3-sulfopropyl)-1H-benz[e]indolium, Inner Salt, Sodium Salt, Reaction Product With PEG 3400 α,ω-diamine The title product was produced analogously to that of Example 3 using PEG 10,000 α,ω-diamine.

EXAMPLE 5

Preparation of the bis(thioether) 2:1 dye:polymer Reaction Product Between 2-[2-[2-chloro-3-[[1,3-dihydro-1,1,-dimethyl-3-(3-sulfopropyl)-2H-benz [e] indol-2-ylidene]ethylidene]-5-(ethoxycarbonyl)-1-cyclohexen-1-yl]ethenyl]-1,1-dimethyl-3-(3-sulfopropyl)-1H-benz[e]indolium, Inner Salt, Sodium Salt and Disodium PEG$_{3,4000}$-α,ω-dithiolate, (NC 100448)

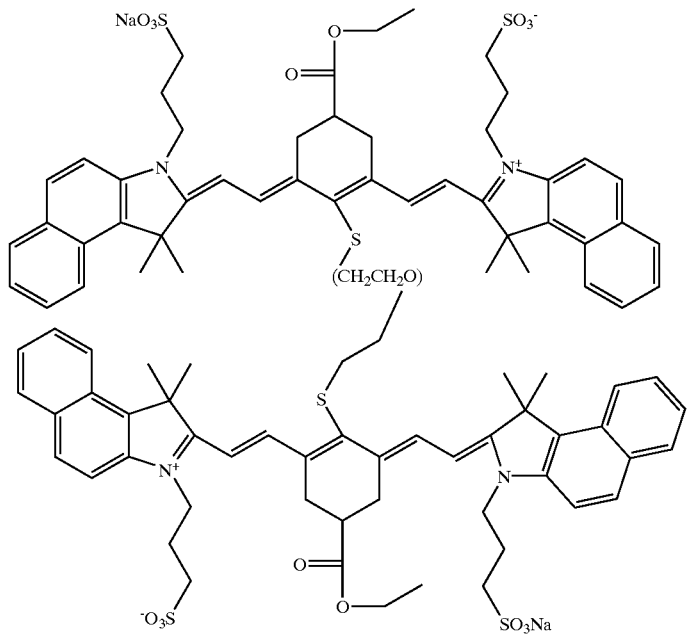

A solution of 1.9 g of 3,400 molecular weight poly (ethylene glycol)-α,ω-dithiol from Shearwater Polymers, Inc. in 8.5 ml of dry and nitrogen-sparged dimethylformamide was treated with 0.1 g of 50% sodium hydride, and then added dropwise under nitrogen at room temperature over 15 minutes to a stirred solution of 0.89 g of 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz[e]indolium in 9 ml of nitrogen-sparged, anhydrous dimethylformamide. After two and one. half hours, the reaction mixture was treated with excess carbon dioxide, the solvent was evaporated, and the desired 2:1 dye:polymer adduct was isolated by column chromatography (SiO2:15% methanol in chloroform).

Biodistribution results are presented in FIGS. 1a (one hour post-dosing) and 1b (three hours post-dosing).

EXAMPLE 6

Gas Bubbles Encapsulated In a Light Absorbing Shell

A cyanine dye of the general structure of formula II with n=3, X=C(CH$_3$)$_2$, R$_1$=H, R$_2$=C$_{18}$H$_{20}$ and Z=Cl$^-$ is prepared by well-known art (Southwick, et al., 1990, Cytometry, 11, pp. 418–430; Mujumdar, S. R. et al., 1996, Bioconjugate Chem., 7, pp. 356–363). To a slurry of 20 μg of the dye in 1 ml of a 5% solution of propylene glycol-glycerol in water is added 5 mg of phosphatidylserine (90–99.9 mol %). The dispersion is heated to not more than 80° C. for 5 minutes then is cooled to ambient temperature. The dispersion (0.8 ml) is transferred to a vial (1 ml) and the head space is flushed with perfluorobutane. The vial is shaken in a cap mixer for 45 seconds, then the sample is put on a roller table. After centrifugation, the infranatant is exchanged with water and the washing is repeated.

EXAMPLE 7

Photoacoustic Imaging With Infrared Radiation and NC100448

The dry contrast agent (4.6 mg) was dissolved immediately before use in 1 ml phosphate buffered saline (Delbecco's buffer). The solution was doubly filtered through a syringe filter with a pore size of 0.45 μm and then was stored in the dark before injection.

The test animals were hairless, immunocompetent mice weighing about 23 g, which were anaesthetized I. m. with 5 μl xylazine (Rompun) and 10 μl ketamine prior to the measurements.

The irradiating light was produced by an alexandrite laser operating at a frequency of 750 nm. The light beam was attenuated with a neutral density filter so that the energy imparted by each pulse to the skin of the mice was less than 50 millijoules.

For imaging, the mouse rested on the lithium niobate acoustic transducer. The photoacoustic signal was detected after it passed to the opposite side of the mouse from incident radiation. The signal was detected after it passed through the body of the mouse to the opposite side from the point of irradiation.

Before injection of the contrast agent, the first mouse was positioned on its back on the transducer so as to maximize the internal signal when the skin above the liver was irradiated. The light beam was much smaller than the liver itself, and the detected signal was probably from blood vessels within the liver. The injected dose was 100 µl injected intravenously into the tail vein with a 26 gauge needle. Immediately following injection, the mouse was again positioned for a maximum signal. The maximum detected signal from the blood vessels of the liver was 5 to 10 times larger than that obtained prior to injection of the agent as is shown in FIG. 2.

FIG. 2 shows one-dimensional images obtained from a hairless, immunocompetent mouse before and after injection of a solution of NC100448 into the tail vein. The right-hand edge of each trace corresponds to the point at which the skin was irradiated. The absorbed light generated a pressure wave that passed through the body of the mouse and was detected with a transducer generating an electrical signal measured in millivolts. The bottom axis shows the time following the radiation pulse. The components of the pressure wave that were generated within the body of the mouse were those first detected and appear to the left of the trace. The component of the trace generated on the skin was detected later and appears at the right. The depth within the mouse of the point of origin of the pressure wave is proportional to the time of arrival of the corresponding pressure pulse. The scale is shown at the top of the figure.

EXAMPLE 8

Photoacoustic Imaging With X-rays and Barium Sulfate

Monochromatic X-rays with a photon energy of 20 to 30 keV are obtained with a double crystal monochromator using white X-rays from a sychrotron. The beam intensity is modulated by a rotating lead plate chopper with a frequency of 10 Hz. The sample chamber is a cylindrical cell with a volume of about 0.5 ml in a saline bath which has two beryllium windows. The photon flux into the sample chamber is measured with an ionization chamber placed in front.

The amplitude of the photoacoustic signal, normalized to the photon flux, is measured when the sample chamber contains the saline solution and when it contains a barium sulfate suspension. Such suspensions are readily available as contrast agents for imaging of the gastrointestinal tract. Other suspensions of particles containing heavy metals are also suitable. The signal is larger when the chamber contains the contrast agent.

EXAMPLE 9

Photoacoustic Imaging With X-rays and Iodixanol

Monochromatic X-rays with a photon energy of 20 to 30 keV are obtained with a double crystal monochromator using white X-rays from a sychrotron. The beam intensity is modulated by a rotating lead plate chopper with a frequency of 10 Hz. The sample chamber is a cylindrical cell with a volume of about 0.5 ml in a saline bath which has two beryllium windows. The photon flux into the sample chamber is measured with an ionization chamber placed in front.

The amplitude of the photoacoustic signal, normalized to the photon flux, is measured when the sample chamber contains the saline solution and when it contains a solution of iodixanol in PBS. Iodixanol is a known soluble contrast agent. Other soluble contrast agents containing iodine may also be used. The signal is larger when the chamber contains the contrast agent.

EXAMPLE 10

Photoacoustic Imaging With Microwaves and Suspended Superparamagnetic Particles

Microwave radiation is generated by a pulsed klystron operating at 2.45 GHz. The klystron is coupled to a waveguide terminated in a horn antenna at 30 cm from the sample container, which is made of Teflon. The sample container is 1 cm in diameter and is immersed in a bath of liposyn.

The acoustic signal following each pulse of radiation is detected with a lithium niobate acoustic transducer placed on the wall of the bath. The transit time of the acoustic signal from the sample to the wall of the bath is proportional to the distance of the sample from the wall of the bath.

The amplitude of the signal obtained when the sample container contains the liquid suspension of superparamagnetic particles is greater than that obtained when the sample container contains PBS buffer.

EXAMPLE 11

Formulation of Indocyanine Green in a Liposome

Indocyanine Green (ICG) was added to a liposome suspension formed from 8.2% lecithin (phosphatidyl choline), 0.8% dimyristalphosphatidylglycerol, and 0.1% of a nonionic, polymeric surfactant, P-79, which is designed to impart prolonged blood pool residence to the liposome. The phospholipids and the surfactant were mixed in water using ultrasonic energy from a probe sonicator (Bransonic Sonifier 450, 90% duty cycle, output 10). Liposomes were prepared using a Microfluidics M110S microfluidizer at 14,000 PSI and 4 passes through the interaction chamber of the phospholipid mixture. The resulting liposomes were approximately 100 nm in average. diameter as determined by light scattering and remained the same size after autoclave sterilization. In addition, these liposomes were able to pass through a sterile filter (i.e., 0.2 micron pore size). Addition of ICG in a sufficient amount to make the suspension approximately 7 mg/ml in ICG did not alter the physical characteristics of the liposomal suspensions. After sterilization under a nitrogen atmosphere, these ICG liposomes were stable for at least 6 weeks at room temperature.

Assessment of the spectral properties of the liposomal ICG relative to ICG dissolved in water or saline demonstrated the impact of the liposomal environment. Both the excitation maximum wavelength and emission wavelength were shifted to lower energies (i.e., higher wavelengths) relative to the homogeneous water solutions. In addition, careful measurements of quantum yield demonstrate at least a 4 fold increase in quantum yield of the liposome ICG relative to the aqueous ICG solutions. Nevertheless, it is expected that radiation with light of the absorbency maximum of ICG will result in the generation of pressure wave emanating from the interface between the liposome and the bulk aqueous milieu which will be detectable by an acoustic signal for imaging applications.

EXAMPLE 12

Liposomal Suspension of X-ray Absorbing Dye for Photoacoustic Imaging

Liposomes (CTP-10) of phosphatidyl choline and phosphatidyl serine in a molar ratio of 10 to 1 were prepared by extrusion through stacked 1 micron pore size filters under pressure. These liposomes were prepared in a solution which contained 400 mg/ml iodixanol, an iodinated, soluble X-ray contrast agent. Thus, each liposome contained a significant amount of iodinated contrast agent within the internal aqueous pool of the liposome. This formulation of liposome encapsulated CT X-ray contrast agent (i.e. iodixanol) was administered to -rabbits as a single bolus of 150 mg Iodine/kg, a divided bolus of 2×75 mg Iodine/kg, and a 10 minute infusion of 80 mg I/minute (total dose=800 mg I or approximately 265 mg Iodine/kg at 1 ml/min). X-ray imagining was carried out on a GE spiral CT scanner at Palo Alto Veterans Hospital, Palo Alto, Calif. Neither the single bolus nor the divided bolus afforded significant blood opacification beyond 1 minute post administration. The infusion, however, provides useful opacification of the blood during the infusion as well. as liver enhancement. Even at 5 minutes into tne infusion, the contrast in the aorta is approximately 125 HU, at least 50 HU above background opacification levels.

With respect to photoacoustic imaging, the CT data clearly show the levels of contrast agent present within the various structures (i.e. liver, blood). The current belief in the field is that every 30 HU equates with approximately 1 mg/g of iodine or more approximately 2 mg contrast agent/g of tissue. Thus, contrast agent levels up to 8–10 mg/g tissue are achieved in the above dosing regimens. It is expected that acoustic detectors located on or near the body of the rabbit would pick up the signals generated from the expansion of the liposome itself upon exposure to diagnostic X-rays due to heat within the liposome from the absorption of X-rays by the X-ray contrast agent. If the X-ray beam could be modulated either electronically or via a shutter, the photoacoustic signal could be used for depth profiling as well as planar imaging.

EXAMPLE 13

Preparation of a Stable Emulsion of Sudan III

Sudan III (also known as D&C Red No 17, Solvent Red 23, Cerasin Red) is very water insoluble but soluble in sesame oil, a well known oil for parenteral oil-in-water emulsions (e.g. Intralipid, Liposyn, etc.) and has a maximum wavelength of light absorption of 507 nm. Thus, an emulsion of Sudan III was prepared as follows: A saturated solution of Sudan III in sesame oil was prepared by gently rotating the container over. the weekend (approx 72 hr). The oil solution was then filtered through a 5 micron syringe filter followed by a 0.8 micron filter to remove undissolved solid Sudan III. The resulting saturated solution was then emulsified in water at a ratio of 10% "oil" to 90% aqueous surfactant solution using ultrasonic energy followed by micro-fluidization at approximately 14,000 PSI until a constant droplet size was achieved. Droplet size was measured by light scattering using a Horiba 910 light scattering device and a volume weighted average. The resulting emulsions were also sterilized by traditional steam sterilization and the droplet size measured again with the following results:

| | | Average Droplet Size (nm) | |
|---|---|---|---|
| | Formulation | Before Autoclaving | After Autoclaving |
| 1. | 1.2% lecithin, 0.3% F68 | 787 | 909 |
| 2. | 1.2% lecithin, 2% P79 | 141 | 199 |
| 3. | 0.8% lecithin, 3% P79 | 122 | 128 |

P79, described in Example 2k of International Patent Publication WO 96/07434, is a PEG-double ester of molecular weight about 10,000 and formula: $CH_3(CH_2)_{13}COO(CH_2)_{15}COO((CH_2)_2O)_nCH_3$. P79 is a polymeric surfactant which appears to add greatly to the ability to make a small emulsion droplet of sesame oil saturated with Sudan III. The resulting rose-colored emulsion is stable on the shelf.

It is expected that, upon irradiation with light of 507 nm, these oil droplets will expand and generate a pressure wave from their water interface due to the release of heat from the excited dye after light absorption. Thus, a modulated light source will afford depth profiling by acoustic detection while continuous irradiation will allow photoacoustic microscopy.

EXAMPLE 14

Liposomes were prepared as in Example 11 above with the addition of water soluble absorbing dye such as those described in U.S. patent application Ser. No. 08/848,586 entitled "Method of tumor treatment" filed on Apr. 29, 1997 in the name of William Anthony Sanderson, and in International Patent Application No. PCT/GB98/01245. Again, the liposomes themselves would generate a pressure wave as a result of light absorption at the appropriate wavelength of the dye encapsulated within the aqueous pool of the liposome. This pressure wave would be useful to acoustic imaging, thus completing the photoacoustic imaging paradigm.

EXAMPLE 15

Preparation of a Superparamagnetic Particle Suspension

A particle suspension was prepared according to the method described in Example 1 of WO 97/25073, by the following method steps:

A. Preparation of Starch Solution

1. Suspend 50 grams of soluble potato starch (CAS No. 9005-84-9) in 850 grams of boiling deionized water and mix.
2. Bring to the boil and immediately on boiling place the starch solution in a 55° C. water bath.

B. Addition of Iron and Ammonium Hydroxide to Starch

1. Dissolve 9.0 grams of $FeCl_3.6H_2O$ and 3.3 grams of $FeCl_2.4H_2O$ (2:1 molar ratio FeIII to FeII) in a total volume of 50 mL of deionized water.
2. After starch solution has cooled to a steady 55° C., pour the iron solution into the starch solution, mix thoroughly and add 50 ml of 30% (conc.) $NH_4OH$.
3. Heat the resulting solution so as to increase the temperature to 89° C. over 2 hours and maintain at 89° C. for a further 50 minutes.
4. After the 170 minute heating on the water bath, chill overnight at 4° C.

C. Washing Procedure

Wash by pumping cold deionized water through settled suspension until pH is less than 8.5.

D. Oxidative Cleavage with Sodium Hypochlorite

A dose titration of the amount of sodium hypochlorite (hypo) per gram of gel is done on a new lot to optimize production. Magnetic particle production is assessed by photon correlation spectroscopy (PCS) for size and dispersity, and by determination of water proton relaxation rates.

a. Treat 1.8 mls of 5% hypochlorite per 12.5 mgs Fe/5 gms of suspension. Adjust volume of hypochlorite for concentration of available chlorine and mgs Fe in 5 grams of suspension.

b. Weigh out suspension, add hypochlorite and heat in water bath at 70° C. for 45 minutes.

c. Add 8M urea (0.8 ml/5 gms of suspension) after heating. Urea inactivates excess hypochlorite.

d. Diafilter using a membrane (MW cutoff<100 kD) until all free Fe and CHO is removed.

A black suspension resulted which was found to contain approximately 8% iron (determined by ICP).

EXAMPLE 16

Thermal Response of a Superparamagnetic Particle Suspension to Microwave Radiation An experiment was conducted to demonstrate that a superparamagnetic particle suspension gives an enhanced response to microwave radiation compared with water. A 125 ml glass Erlenmeyer flask was charged with 100 ml of a superparamagnetic particle suspension prepared as described in Example 15 above. An identical flask was charged with 100 ml of distilled water. The two flasks were placed on the rotatable carousel stage inside a Sharp Carousel Household Microwave Oven (Model R-5A97). The microwave oven was then operated at power level 5 (50% of maximum power) for 20 second intervals, during which time the carousel stage rotated. Between the 20 second operating intervals, the temperature of each sample was measured by quickly removing the sample, measuring the temperature with a thermometer, and quickly returning it to the microwave oven. The temperatures were recorded and the 20 second operating cycle quickly repeated. After a number of repeats of this process the experiment was terminated. To confirm the trend observed in the results, the entire experiment was repeated with a second sample of the superparamagnetic particle suspension and a second sample of distilled water. The results are shown below:

| Cumulative Elapsed Microwave Exposure Time | Temp. of Superparamagnetic Particle Suspension | Temp. of Distilled Water Sample |
|---|---|---|
| Experiment A | | |
| 0 sec | 23° C. | 23° C. |
| 20 sec | 30° C. | 31° C. |
| 60 sec | 41° C. | 39° C. |
| 80 sec | 51° C. | 47° C. |
| 120 sec | 75° C. | 62° C. |
| 180 sec | 98° C.* | 83° C. |
| Experiment B | | |
| 0 sec | 23° C. | 23° C. |
| 20 sec | 32° C. | 31° C. |
| 60 sec | 48° C. | 47° C. |
| 80 sec | 57° C. | 55° C. |
| 100 sec | 67° C. | 62° C. |
| 120 sec | 74° C. | 68° C. |
| 140 sec | 81° C. | 73° C. |
| 160 sec | 93° C. | 81° C. |
| 180 sec | 98° C.* | 84° C. |

*in each case at 180 sec there was some boiling of the superparamagnetic particle suspension.

EXAMPLE 17

Preparation of Liposome Encapsulated Indocyanine Green

Solution A contained 435.06 mg/ml Iohexol, 10.88 mg/ml P79, and 6.44 mg/ml ICG in 25 ml NanoPure water.

Solution B consisted of 4.1% Tris-HCL and 0.41% EDTA in NanoPure water.

To 23.56 ml of Solution A was added 1.44 grams of a 10:1 mixture of phosphatidyl choline and phosphatidyl serine. The resulting solution was heated to 80° C. with stirring until the phospholipids transformed from the solid to the gel state. The mixture was then heated and stirred for 20 minutes. There was considerable foaming. The water lost to evaporation was replaced. The hot solution was homogenized for 20 seconds (24,000 rpm) and was then immediately extruded at 80° C. through seven stacked 1 micron polycarbonate membranes at 100–150 psi. Some green color remained on the filters. The final product was produced by adding 1 part of Solution B to 40 parts of the extruded mixture. It was frozen and stored 4 days before thawing for 4 hours at room temperature.

EXAMPLE 18

Figure 3:
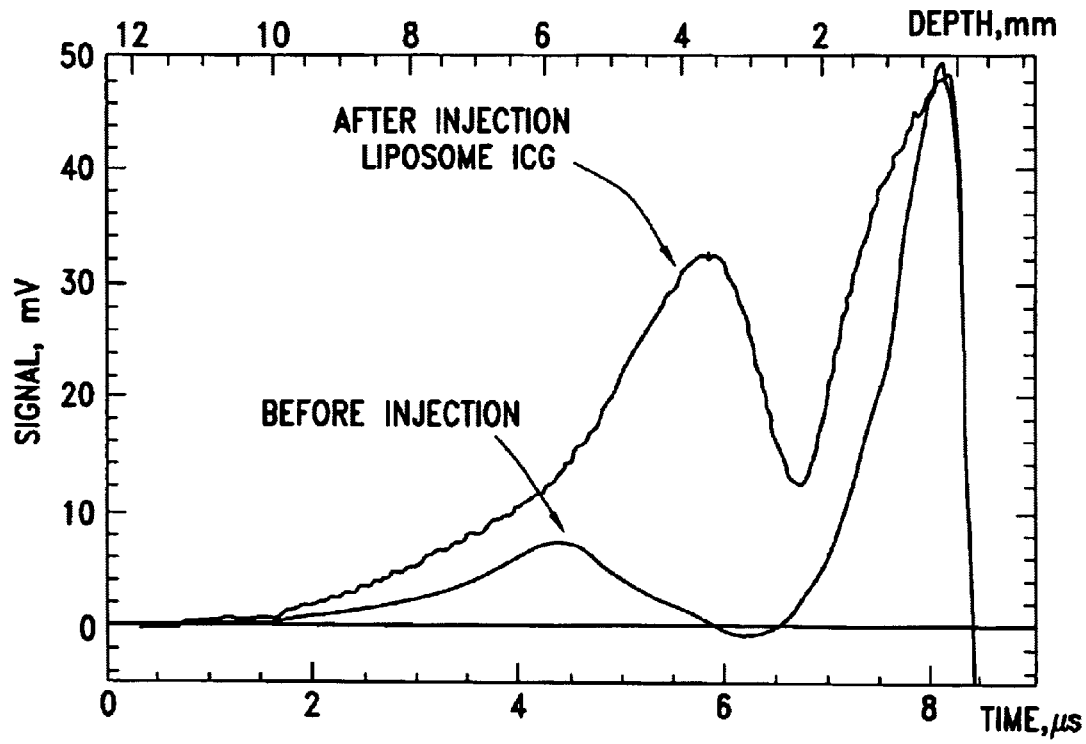
FIG. 3 shows one-dimensional images obtained from a hairless, immunocompetent mouse before and after injection of a liposome suspension of indocyanine green into the tail vein (see Example 18 below).

Photoacoustic Imaging With Infrared Irradiation and Liposome Encapsulated Indocyanine Green The imaging procedure was the same as that described in Example 7. After the maximum signals from the area of the livers and from the flanks was found, two mice were each injected with 100 μl of liposomal indocyanine green. Massage was used to move the viscous solution from the tail vein into the vasculature as a whole. The maximum signals from the livers and flanks were again recorded. The signal enhancement produced by the contrast agent was 5- to 6-fold, as shown in FIG. 3.

What is claimed is:

1. A method of generating an image of an animate human or non-human animal body or part thereof, said method comprising administering to said body a physiologically tolerable contrast agent comprising a pressure inducing component, exposing said body to radiation, detecting pressure waves generated in said body by said radiation and generating an optoacoustic image therefrom of at least a part of said body containing the administered contrast agent.

2. A method of generating an image of an animate human or non-human animal body or part thereof, said method comprising administering to said body a physiologically tolerable contrast agent comprising a pressure inducing component and a radiation absorbing component, exposing said body to radiation, detecting pressure waves generated in said body by said radiation and generating an optoacoustic image therefrom of at least a part of said body containing the administered contrast agent.

3. A method as claimed in claim 2 wherein X-ray or gamma ray radiation with a wavelength of less than 0.1 μm is used.

4. A method as claimed in claim 3 wherein said radiation absorbing component comprises an element with atomic number greater than 20.

5. A method as claimed in claim 4 wherein said radiation absorbing component comprises an element selected from barium, tungsten, iodine, bromine, bismuth and lanthanide elements.

6. A method as claimed in claim 4 wherein said radiation absorbing component includes a highly iodinated aromatic compound.

7. A method as claimed in claim 3 wherein said radiation absorbing component includes an iodinated compound containing at least one atom of iodine per molecule.

8. A method as claimed in claim 7 wherein said radiation absorbing component includes an iodinated compound containing at least three atoms of iodine per molecule.

9. A method as claimed in claim 7 wherein said radiation absorbing component includes an iodinated compound containing at least six atoms of iodine per molecule.

10. A method as claimed in claim 3 wherein the radiation absorbing component is in the form of a suspension of solid particles in a physiologically acceptable liquid.

11. A method as claimed in claim 10 wherein the particles have diameters of 100 to 500 nm.

12. A method as claimed in claim 3 wherein the radiation absorbing component is in the form of a solid, liquid or gaseous material encapsulated into micelles or liposomes.

13. A method as claimed in claim 12 wherein the gaseous material is xenon.

14. A method as claimed in claim 3 wherein the contrast agent is in the form of a suspension of particles of a ceramic material selected from $Co_2O_3$, $MnO_2$, NiO and CuO, in a physiologically acceptable liquid.

15. A method as claimed in claim 2 wherein said radiation absorbing component includes a dye compound.

16. A method as claimed in claim 15 wherein said dye compound is selected from the group comprising cyanine dyes, squarylium dyes, croconium, phthalocyanine dyes, naphthalocyanine dyes, xanthene dyes, dibenzxanthene dyes, merocyanine dyes, triphenylmethane dyes or porphyrins.

17. A method as claimed in claim 15 wherein said dye compound has the formula I:

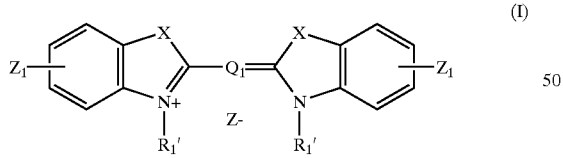

(I)

wherein
each $Z_1$ is independently selected from the group consisting of:
hydrogen,
a methyl group optionally substituted with a substituent selected from the group consisting of hydroxyl, carboxyl, sulfonate, phosphonate, and poly(alkylene oxidyl) such as ω-hydroxypoly(ethylene oxidyl) and ω-methoxypoly(ethylene oxidyl) the molecular weights of which can be up to about 50,000,
an ethyl group optionally substituted with one or two substituents selected from the group consisting of hydroxyl, carboxyl, sulfonate, phosphonate, and poly(alkylene oxidyl) such as ω-hydroxypoly(ethylene oxidyl) and ω-methoxypoly(ethylene oxidyl) the molecular weights of which can be up to about 50,000,
an ethylene group optionally substituted with one or two substituents selected from the group consisting of hydroxyl, carboxyl, sulfonate, phosphonate, and poly(alkylene oxidyl) such as ω-hydroxypoly(ethylene oxidyl) and ω-methoxypoly-(ethylene oxidyl) the molecular weights of which can be up to about 50,000,
a $C_{3-16}$ alkyl group, the alkyl portion of which is optionally substituted as defined above,
a $C_{1-16}$ alkoxyl ether group, the alkyl portion of which is optionally substituted as defined above,
a $C_{1-16}$ carboxyalkyl estergroup, the alkyl portion of which is optionally substituted as defined above,
a $C_{1-16}$ oxycarbonylalkyl ester group, the alkyl portion of which is optionally substituted as defined above,
a $C_{1-16}$ carbonylaminoalkyl amide group, the alkyl portion of which is optionally substituted as defined above,
a $C_{1-16}$ aminocarbonylalkyl amide group, the alkyl portion of which is optionally substituted as defined above,
a carboxylic acid group which may be a carboxylate group,
a sulfonate group,
a hydroxyl group,
a phosphate group,
a $C_{1-16}$ sulfonamidoalkyl group, the alkyl portion of which is optionally substituted as defined above,
a $C_{1-16}$ aminosulfonylalkyl group, the alkyl portion of which is optionally substituted as defined above,
a $C_{1-16}$ aminocarbonylaminoalkyl urea group, the alkyl portion of which is optionally substituted as defined above,
a $C_{1-16}$ aminothiocarbonylaminoalkyl thiourea group, the alkyl portion of which is optionally substituted as defined above,
a phenyl-$C_{1-16}$-alkyl group, the alkyl portion of which is optionally substituted as defined above,
a phenoxy-$C_{1-16}$-alkyl group, the alkyl portion of which is optionally substituted as defined above,
a $C_{1-16}$ phenyloxyalkyl group, the alkyl portion of which is as defined above,
an oxyphenoxy-$C_{1-16}$-alkyl group, the alkyl portion of which is optionally substituted as defined above,
a poly(alkylene oxidyl) group such as hydroxypoly(ethylene oxidyl) and methoxypoly(ethylene oxidyl) with a molecular weight up to about 50,000,
and an annulated aromatic ring which comprises a benz[e]aromatic ring, a benz[f]aromatic ring, or a benz[g]aromatic ring, where e, f, and g are defined relative to the indole structure as a template and each of which ring may be substituted by $C_{1-16}$ alkyl, $C_{1-16}$ alkoxyl, carboxyl, sulfonate, sulfonamido, phenyl, poly(alkylene oxidyl) or phenoxyl groups as defined above;
each $R_1'$ is independently selected from the group consisting of methyl and a $C_{2-16}$ alkyl group including a substituted alkyl group where alkyl is optionally substituted as defined above,
each X is independently selected from the group consisting of O, N—$R_1'$, S, Se, Te, CH=CH, and $(CH_3)_2C$; and $Q_1$ is selected from the group consisting of:
$(CH=CH)_n$ where n has a value of 1 to 6,

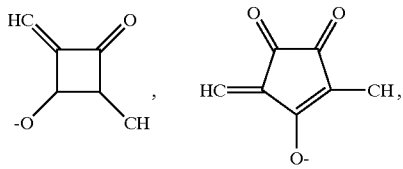

and

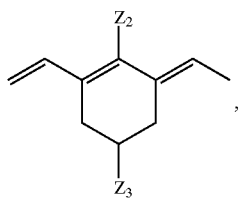

where $Z_2$ is selected from the group consisting of H, chloro, O-alkyl, S-alkyl, where alkyl is optionally substituted as defined above, O-poly(alkylene oxidyl), S-poly(alkylene oxidyl), where poly(alkylene oxidyl) is as defined above and also includes poly(alkylene oxide) groups to which another dye is attached at the w-end, O-phenyl, S-phenyl, wherein the phenyl groups may be substituted with alkyl groups optionally substituted as defined above, O-alkyl groups as defined above, S-alkyl groups as defined above, aminothiocarbonylaminoalkyl groups, and aminothiocarbonylamino-phenyl groups, and where $Z_3$ is selected from the group consisting of H, carboxylate, and carboxyalkyl where alkyl is as defined above, carbonylaminoalkyl where alkyl is as defined above, and carbonylaminophenyl where phenyl is as defined above, and

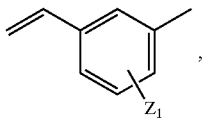

and $Z^-$ is a physiologically tolerable counterion.

18. A method as claimed in claim 17 wherein the physiological counterion is I, Br, Cl or OAc.

19. A method as claimed in claim 15 wherein said dye compound has the formula II:

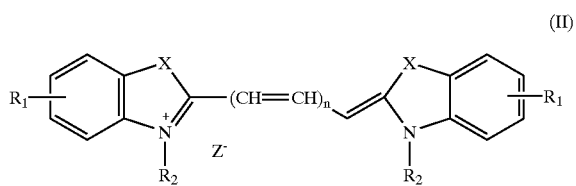

wherein n is an integer having a value of 1 to 6;

each $R_1$, which may be the same or different, represents a hydrogen atom or a solubilizing group, or adjacent $R_1$ substituents together with the ring carbons to which they are attached may form a ring structure, which may be a 5 or 6-membered ring;

each $R_2$, which may be the same or different, represents a hydrogen atom or a lipophilic group, alternatively, each $R_2$ may be an optionally unsaturated $C_{2-8}$ alkyl group which is attached to one or more solubilizing groups;

each X, which may be the same or different, each represents O, S, —CH=CH— or $C(R_3)_2$ in which each $R_3$, which may be the same or different, represents a hydrogen atom or a methyl or ethyl group;

Z is a physiologically tolerable counterion.

20. A method as claimed in claim 19 wherein the physiological counterion is I, Br, or Cl.

21. A kit of parts for a method as claimed in claim 2 comprising both a radiation absorbing component according to claim 15 and a pressure-inducing component selected from a gas, a gas precursor or an oil-in-water emulsion droplet, said components being suitable for separate, administration (simultaneously or sequentially) to an animate human or non-human animal.

22. A kit of parts for a method as claimed in claim 2 comprising both a radiation absorbing component according to claiml 4 and a pressure-inducing component selected from a gas, a gas precursor or an oil-in-water emulsion droplet, said components being suitable for separate, administration (simultaneously or sequentially) to an animate human or non-human animal.

23. A kit of parts for a method as claimed in claim 2 comprising both a radiation absorbing component according to claim 7 and a pressure-inducing component selected from a gas, a gas precursor or an oil-in-water emulsion droplet, said components being suitable for separate, administration (simultaneously or sequentially) to an animate human or non-human animal.

24. A kit of parts for a method as claimed in claim 2 comprising both a radiation absorbing component according to claim 10 and a pressure-inducing component selected from a gas, a gas precursor or an oil-in-water emulsion droplet, said components being suitable for separate, administration (simultaneously or sequentially) to an animate human or non-human animal.

25. A kit of parts for a method as claimed in claim 2 comprising both a radiation absorbing component according to claim 12 and a pressure-inducing component selected from a gas, a gas precursor or an oil-in-water emulsion droplet, said components being suitable for separate, administration (simultaneously or sequentially) to an animate human or non-human animal.

26. A method as claimed in claim 1 wherein radiation with a wavelength of 300–1300 nm is used.

27. A method as claimed in claim 26 wherein radiation with a wavelength of 600–1300 nm is used.

28. A method as claimed in claim 26 wherein radiation with a wavelength of 625–1200 nm is used.

29. A method as claimed in claim 26 wherein radiation with a wavelength of 650–1000 nm is used.

30. A method as claimed in claim 1 wherein X-ray or gamma ray radiation with a wavelength of less than 0.1 μm is used.

31. A method as claimed in claim 30 wherein the contrast agent is in the form of a suspension of solid or liquid particles in a physiologically acceptable liquid.

32. A method as claimed in claim 31 wherein the particles have diameters of 100 to 500 nm.

33. A method as claimed in claim 30 wherein the contrast agent is in the form of a solid or liquid material encapsulated into micelles or liposomes.

34. A method as claimed in claim 1 wherein microwave radiation with a frequency of from 0.3 GHz to 30 GHz is used.

35. A method as claimed in claim 34 wherein the contrast agent is in the form of a suspension of superparamagnetic particles in a physiologically acceptable liquid.

36. A method as claimed in claim 35 wherein the particles have diameters of 5 to 30 nm.

37. A method as claimed in claim 1 wherein short pulses of radiation are used.

38. A method as claimed in claim 1 wherein said contrast agent comprises an active targeting ligand.

39. A method as claimed in claim 38 wherein the active targeting ligand is capable of binding to a dihydrofolate reductase receptor.

40. A method as claimed in claim 1 wherein said pressure-inducing component is a gas precursor.

41. A method as claimed in claim 40 wherein said gas precursor is selected from graphite, aminomalonates, carbonates, bicarbonates, physiologically acceptable diazonium compounds, carbonate esters containing groupings of the type $-CO-O-CR^1R^2-O-CO-OR^3$, and β-ketoacids.

42. A Method as claimed in claim 1 wherein said pressure-inducing component is an oil-in-water emulsion droplet.

43. A method as claimed in claim 42 wherein said emulsion droplet comprises a light-absorbing, lipophilic dye.

44. A method as claimed in claim 43 wherein said light-absorbing particles comprise particles of graphite and/or surface-modified pigment particles.

45. A method as claimed in claim 42 wherein said emulsion droplet contains hydrophobic light-absorbing particles.

46. A method as claimed in claim 1 wherein said contrast agent comprises at least one chromophoric group attached to a surfactant molecule.

47. A method as claimed in claim 1 wherein said pressure-inducing component is a gas.

48. A method as claimed in claim 47 wherein said gas is xenon or a perfluorocarbon.

* * * * *